(12) United States Patent
Beckmann et al.

(10) Patent No.: US 7,235,571 B2
(45) Date of Patent: Jun. 26, 2007

(54) HETEROCYCLIC AMIDE AND IMINE DERIVATIVES, PROCESSES FOR THEIR PREPARATION, COMPOSITIONS COMPRISING THEM AND THEIR USE AS PESTICIDES

(75) Inventors: Marion Beckmann, Wiesbaden (DE); Oswald Ort, Glashütten (DE); Uwe Döller, Rodgau (DE); Gerhard Krautstrunk, Bad Vilbel (DE); Wolfgang Schaper, Diedorf (DE); Peter Lümmen, Idstein (DE); Daniela Jans, Bad Homburg v. d. H. (DE); Waltraud Hempel, Liederbach (DE); Jutta Maria Waibel, Frankfurt (DE); Barbara Lörkens, Kriftel (DE)

(73) Assignee: Merial Limited, Duluth, GA (US)

( * ) Notice: Subject to any disclaimer, the term of this patent is extended or adjusted under 35 U.S.C. 154(b) by 351 days.

(21) Appl. No.: 10/811,578

(22) Filed: Mar. 29, 2004

(65) Prior Publication Data

US 2004/0192712 A1   Sep. 30, 2004

Related U.S. Application Data

(63) Continuation of application No. 10/246,220, filed on Sep. 18, 2002, now abandoned.

(30) Foreign Application Priority Data

Sep. 24, 2001   (DE) ................. 101 46 873

(51) Int. Cl.
*C07D 213/78* (2006.01)
*C07D 401/12* (2006.01)
*A01N 43/40* (2006.01)
*A01N 43/824* (2006.01)

(52) U.S. Cl. ............... 514/355; 544/316; 544/317
(58) Field of Classification Search ........... 546/316, 546/317; 514/355
See application file for complete search history.

(56) References Cited

U.S. PATENT DOCUMENTS 6,028,101 A   2/2000   Phillion et al. ............ 514/469
6,117,821 A   9/2000   Tice et al.

FOREIGN PATENT DOCUMENTS

DE    36 00 288 A1    7/1987
EP    0 434 097 A1    6/1991
EP    0 580 374 A     1/1994
EP    0 580 374 A1    1/1994
JP    62-181261   *   8/1987
JP    3-68550     *   3/1991
WO    WO 99/16744     4/1999
WO    WO 01/09104 A1  2/2001
WO    WO 01/70692 A2  9/2001

OTHER PUBLICATIONS

Yoshida et al., CAPLUS Abstract 108:131590 (corresponds to JP 62-181261), 1988.*
Mori et al., CAPLUS Abstract 115:153116 (corresponds to JP 3-68550), 1991.*
Patent Abstracts of Japan, vol. 12, No. 033, Jan. 30, 1988.
Database WPI, AN 2001-211706, Nov. 29, 2000.
Database Accession No. 347371-46-4, also referred to as XP 002228063; 2000.

* cited by examiner

*Primary Examiner*—Deepak Rao
(74) *Attorney, Agent, or Firm*—Thomas J. Kowalski; Judy Jarecki-Black; Frommer Lawrence & Haug LLP

(57) ABSTRACT

What is described are compounds of the formulae (I) and (II)

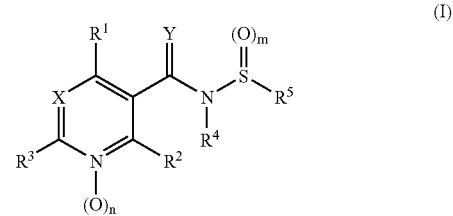

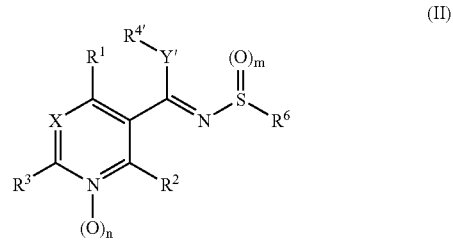

where the symbols and indices have the meanings given in the description.

These compounds are suitable for controlling animal pests.

19 Claims, No Drawings

HETEROCYCLIC AMIDE AND IMINE DERIVATIVES, PROCESSES FOR THEIR PREPARATION, COMPOSITIONS COMPRISING THEM AND THEIR USE AS PESTICIDES

This application is a continuation of application Ser. No. 10/246,220 filed Sep. 18, 2002, now abandoned.

The invention relates to heterocyclic amide and imine derivatives, to processes for their preparation, to compositions comprising them and to their use for controlling animal pests, in particular arthropods, such as insects and acarids, and helminths.

Owing to the enormous damage caused by insects, for example by feeding on useful plants, stored food, wood and textiles, or else by transferring diseases to man, domestic animals and useful plants, the use of insecticides or repellants remains indispensable. Insecticides are an important component of integrated pest control, and their contribution is decisive with respect to harvest yields and yield continuity all over the world.

Substituted carbocyclic and heterocyclic compounds for use as fungicides are known from U.S. Pat. No. 6,028,101. The general formula of the compounds described also includes pyridylamides whose amide nitrogen may be substituted by various groups, inter alia alkylthio. However, there is no concrete disclosure of such compounds.

DE-A-36 00 288 describes the use of selected amides as antidotes for improving the crop plant compatibility of selected herbicidally active sulfonylurea derivatives. The amides used can inter alia be pyridinecarboxylic acid derivatives which are substituted at the amide nitrogen by an alkylthio group. However, there is no concrete disclosure of such compounds.

EP-A434,097 describes a process for developing silver-halide-containing materials for color photography. The developer materials used include inter alia materials comprising components derived from heterocyclic imine derivatives. However, there is no concrete disclosure of compounds which contain pyridyl radicals.

EP-A 0 580 374 discloses trifluoromethylpyridineamides for use as pesticides.

However, since the ecological and economic demands made on modern insecticides are increasing continually, for example with respect to toxicity, selectivity, application rates, formation of residues and favorable manufacture, and there can furthermore be problems, for example with resistance, there is a constant need to develop novel insecticides which, at least in some areas, have advantages over those of the prior art.

It has been found that compounds of the formulae (I) and (II), if appropriate also as salts, have a good activity spectrum against animal pests and at the same time good compatibility with plants and favorable toxicological properties with respect to mammals and aquatic animals.

Accordingly, the present invention provides amides of the formula (I) and salts thereof

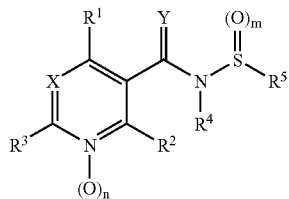

(I)

where the symbols and indices are as defined below:
X is =CH— or =N—;
Y is =O or =S;
n is 0 or 1;
m is 0, 1 or 2;
$R^1$ is $(C_1-C_6)$-alkyl, $(C_1-C_6)$-haloalkyl, —S(halogen)$_5$ or halogen, where one or two $CH_2$ groups may be replaced by —O— or —S— or —N$(C_1-C_6)$-alkyl, with the proviso that heteroatoms may not be adjacent;
$R^2$, $R^3$ independently of one another are hydrogen, $(C_1-C_6)$-alkyl, $(C_1-C_6)$-haloalkyl or halogen, where one or two $CH_2$ groups may be replaced by —O— or —S— or —N$(C_1-C_6)$-alkyl, with the proviso that heteroatoms may not be adjacent;
$R^4$ is hydrogen, $(C_1-C_{10})$-alkyl, $(C_3-C_{10})$-cycloalkyl, $(C_3-C_{10})$-alkenyl, $(C_3-C_{10})$-alkynyl, $(C_6-C_{14})$-aryl, $(C_3-C_{10})$-heterocyclyl or $(C_1-C_{10})$-alkanoyl, where the radicals mentioned may be unsubstituted or mono- or polysubstituted;
$R^5$ is hydrogen, $(C_1-C_{10})$-alkyl, $(C_3-C_{10})$-alkenyl, $(C_3-C_{10})$-alkynyl, $(C_3-C_8)$-cycloalkyl, $(C_4-C_8)$-cycloalkenyl, $(C_8-C_{10})$-cycloalkynyl, aryl or heterocyclyl, where the radicals mentioned may be unsubstituted or mono- or polysubstituted;
except for compounds of the formula (I), in which X is =CH—, m is 1 or 2 and $R^5$ is unsubstituted or substituted $(C_1-C_{10})$-alkyl.

The invention furthermore provides imine derivatives of the formula (II) and salts thereof

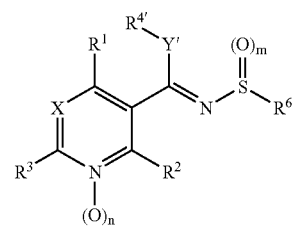

(II)

where the symbols and indices are as defined below:
X is =CH— or =N—, —O—, —S—;
Y' is —O— or —S—;
n is 0 or 1;
m is 0, 1 or 2;

Particular preference is given to those compounds of the formula (I) in which the symbols and indices are as defined below:
X is preferably =CH—;
Y is preferably =O;
m is preferably 0;
n is preferably 0;
$R^1$ is preferably —CF$_3$;
$R^2$ and $R^3$ are preferably hydrogen;
$R^5$ is preferably $(C_1-C_{10})$-alkyl, $(C_2-C_{10})$-alkenyl, $(C_2-C_{10})$-alkynyl, $(C_3-C_8)$-cycloalkyl, $(C_4-C_8)$-cycloalkenyl, $(C_8-C_{10})$-cycloalkynyl, aryl or heterocyclyl, where the radicals mentioned may be unsubstituted or mono- or polysubstituted.

The symbols and indices in the formula (II) are preferably as defined below:
X is preferably =CH—.
Y' is preferably —O—.
m is preferably 0.
n is preferably 0.

$R^1$ is preferably $SF_5$, $(C_1-C_6)$-haloalkyl, in particular $(C_1-C_6)$-alkyl which is mono- or polysubstituted by F and/or Cl, with particular preference $SF_5$, $CF_3$, $CHF_2$ or $CF_2Cl$, with very particular preference $CF_3$.

$R^2$, $R^3$ are preferably hydrogen, halogen, $(C_1-C_6)$-alkyl, $(C_1-C_6)$-alkoxy, $NH(C_1-C_6)$-alkyl, $N(C_1-C_6)_2$-alkyl, with particular preference hydrogen.

$R^{4'}$ is preferably $(C_1-C_6)$-alkyl or $(C_1-C_6)$-alkyl which is mono- or polysubstituted by F and/or Cl, with particular preference $(C_1-C_6)$-alkyl.

$R^6$ is preferably $(C_1-C_{10})$-alkyl, $(C_3-C_8)$-cycloalkyl, aryl, benzyl or heterocyclyl, where the radicals mentioned may be unsubstituted or mono- or polysubstituted.

The substituents on the radicals $R^4$, $R^{4'}$, $R^5$ and $R^6$ are preferably groups $R^7$, as defined below:

$R^7$ are identical or different $R^8$, or two radicals $R^7$ together with the atoms to which they are attached form a three- to eight-membered saturated or unsaturated ring system which is unsubstituted or substituted by one or more radicals $R^8$ and which may also contain further heteroatoms, preferably O, N, S, SO and/or $SO_2$;

$R^8$ are identical or different $R^9$, $R^{10}$, $-C(W)R^9$, $-C(=NOR^9)R^9$, $-C(=NOR^9)R^9$, $-C(=NNR^9{}_2)R^9$, $-C(=W)OR^9$, $-C(=W)NR^9{}_2$, $-OC(=W)R^9$, $-OC(=W)OR^9$, $-C(=W)NR^9R^9$, $-N[C(=W)R^9]_2$, $-NR^9C(=W)OR^9$, $-C(=W)NR^9-NR^9{}_2$, $-C(=W)NR^9-NR^9[C=W)R^9]$, $-NR^9-C(=W)NR^9{}_2$, $-NR^9-NR^9C(=W)R^9$, $-NR^9-N[C(=W)R^9]_2$, $-N[(C=W)R^9]-NR^9{}_2$, $-NR^9-N[(C=W)WR^9]$, $-NR^9[(C=W)NR^9{}_2]$, $-NR^9(C=NR^9)R^9$, $-NR^9(C=NR^9)NR^9{}_2$, $-O-NR^9{}_2$, $-O-NR^9(C=W)R^9$, $-SO_2NR^9{}_2$, $-NR^9SO_2R^9$, $-SO_2OR^9$, $-OSO_2R^9$, $-OR^9$, $-NR^9{}_2$, $-SR^9$, $-SiR^9{}_3$, $-PR^9{}_2$, $-P(=W)R^9{}_2$, $-SOR^9$, $-SO_2R^9$, $-PW_2R^9{}_2$, $-PW_3R^9{}_2$ or two radicals $R^8$ together are $(=W)$, $(=N-R^9)$, $(=CR_2{}^9)$, $(=CHR^9)$ or $(=CH_2)$;

W is $=O$ or $=S$;

$R^9$ are identical or different $(C_1-C_6)$-alkyl, $(C_2-C_6)$-alkenyl, $(C_2-C_6)$-alkynyl, $(C_3-C_8)$-cycloalkyl, cycloalkyl, $(C_4-C_8)$-cycloalkenyl, $(C_3-C_8)$-cycloalkyl-$(C_1-C_4)$-alkyl, $(C_4-C_8)$-cycloalkenyl-$(C_1-C_4)$-alkyl, $(C_3-C_8)$-cycloalkyl-$(C_2-C_4)$-alkenyl, $(C_4-C_8)$-cycloalkenyl-$(C_2-C_4)$-alkenyl, $(C_1-C_6)$-alkyl-$(C_3-C_8)$-cycloalkyl, $(C_2-C_6)$-alkenyl-$(C_3-C_8)$-cycloalkyl, $(C_2-C_6)$-alkynyl-$(C_3-C_8)$-cycloalkyl, $(C_1-C_6)$-alkyl-$(C_4-C_8)$-cycloalkenyl, $(C_2-C_6)$-alkenyl-$(C_4-C_8)$-cycloalkenyl, aryl, heterocyclyl; where the radicals mentioned are unsubstituted or substituted by one or more radicals $R^{10}$ and two radicals $R^9$ together may form a ring system;

$R^{10}$ are identical or different halogen, cyano, nitro, hydroxyl, thio, amino, formyl, $(C_1-C_6)$-alkanoyl, $(C_1-C_6)$-alkoxy, $(C_3-C_6)$-alkenyloxy, $(C_3-C_6)$-alkynyloxy, $(C_1-C_6)$-haloalkyloxy, $(C_3-C_6)$-haloalkenyloxy, $(C_3-C_6)$-haloalkynyloxy, $(C_3-C_8)$-cycloalkoxy, $(C_4-C_8)$-cycloalkenyloxy, $(C_3-C_8)$-halocycloalkoxy, $(C_4-C_8)$-halocycloalkenyloxy, $(C_3-C_8)$-cycloalkyl-$(C_1-C_4)$-alkoxy, $(C_4-C_8)$-cycloalkenyl-$(C_1-C_4)$-alkoxy, $(C_3-C_8)$-cycloalkyl-$(C_2-C_4)$-alkenyloxy, $(C_4-C_8)$-cycloalkenyl-$(C_1-C_4)$-alkenyloxy, $(C_1-C_6)$-alkyl-$(C_3-C_8)$-cycloalkoxy, $(C_2-C_6)$-alkenyl-$(C_3-C_8)$-cycloalkoxy, $(C_2-C_6)$-alkynyl-$(C_3-C_8)$-cycloalkoxy, $(C_1-C_6)$-alkyl-$(C_4-C_8)$-cycloalkenyloxy, $(C_2-C_6)$-alkenyl-$(C_4-C_8)$-cycloalkenyloxy, $(C_1-C_4)$-alkoxy-$(C_1-C_6)$-alkoxy, $(C_1-C_4)$-alkoxy-$(C_3-C_6)$-alkenyloxy, carbamoyl, $(C_1-C_6)$-mono- or -dialkylcarbamoyl, $(C_1-C_6)$-mono- or -dihaloalkylcarbamoyl, $(C_3-C_8)$-mono- or -dicycloalkylcarbamoyl, $(C_1-C_6)$-alkoxycarbonyl, $(C_3-C_8)$-cycloalkoxycarbonyl, $(C_1-C_6)$-alkanoyloxy, $(C_3-C_8)$-cycloalkanoyloxy, $(C_1-C_6)$-haloalkoxycarbonyl, $(C_1-C_6)$-haloalkanoyloxy, $(C_1-C_6)$-alkanoylamino, $(C_1-C_6)$-haloalkanoylamino, $(C_2-C_6)$-alkenoylamino, $(C_3-C_8)$-cycloalkanoylamino, $(C_3-C_8)$-cycloalkyl-$(C_1-C_4)$-alkanoylamino, $(C_1-C_4)$-alkylthio, $(C_3-C_6)$-alkenylthio, $(C_3-C_6)$-alkynylthio, $(C_1-C_6)$-haloalkylthio, $(C_3-C_6)$-haloalkylthio, $(C_3-C_6)$-haloalkynylthio, $(C_3-C_8)$-cycloalkylthio, $(C_4-C_8)$-cycloalkenylthio, $(C_3-C_8)$-halocycloalkylthio, $(C_4-C_8)$-halocycloalkenylthio, $(C_3-C_8)$-cycloalkyl-$(C_1-C_4)$-alkylthio, $(C_4-C_8)$-cycloalkenyl-$(C_1-C_4)$-alkylthio, $(C_3-C_8)$-cycloalkyl-$(C_3-C_4)$-alkenylthio, $(C_4-C_3)$-cycloalkenyl-$(C_3-C_4)$-alkenylthio, $(C_1-C_6)$-alkyl-$(C_3-C_8)$-cycloalkylthio, $(C_2-C_6)$-alkenyl-$(C_3-C_8)$-cycloalkylthio, $(C_2-C_6)$-alkynyl-$(C_3-C_8)$-cycloalkylthio, $(C_1-C_6)$-alkyl-$(C_4-C_8)$-cycloalkenylthio, $(C_2-C_6)$-alkenyl-$(C_4-C_8)$-cycloalkenylthio, $(C_1-C_6)$-alkylsulfinyl, $(C_3-C_6)$-alkenylsulfinyl, $(C_3-C_6)$-alkynylsulfinyl, $(C_1-C_6)$-haloalkylsulfinyl, $(C_3-C_6)$-haloalkenylsulfinyl, $(C_3-C_6)$-haloalkynylsulfinyl, $(C_3-C_8)$-cycloalkylsulfinyl, $(C_4-C_8)$-cycloalkenylsulfinyl, $(C_3-C_8)$-halocycloalkylsulfinyl, $(C_4-C_8)$-halocycloalkenylsulfinyl, $(C_3-C_8)$-cycloalkyl-$(C_1-C_4)$-alkylsulfinyl, $(C_4-C_8)$-cycloalkenyl-$(C_1-C_4)$-alkylsulfinyl, $(C_3-C_8)$-cycloalkyl-$(C_3-C_4)$-alkenylsulfinyl, $(C_4-C_8)$-cycloalkenyl-$(C_3-C_4)$-alkenylsulfinyl, $(C_1-C_6)$-alkyl-$(C_3-C_8)$-cycloalkylsulfinyl, $(C_2-C_6)$-alkenyl-$(C_3-C_8)$-cycloalkylsulfinyl, $(C_2-C_6)$-alkynyl-$(C_3-C_8)$-cycloalkylsulfinyl, $(C_1-C_6)$-alkyl-$(C_4-C_8)$-cycloalkenylsulfinyl, $(C_2-C_6)$-alkenyl-$(C_4-C_8)$-cycloalkenylsulfinyl, $(C_1-C_6)$-alkylsulfonyl, $(C_3-C_6)$-alkenylsulfonyl, $(C_3-C_6)$-alkynylsulfonyl, $(C_1-C_6)$-haloalkylsulfonyl, $(C_3-C_6)$-haloalkenylsulfonyl, $(C_3-C_6)$-haloalkynylsulfonyl, $(C_3-C_8)$-cycloalkylsulfonyl, $(C_4-C_8)$-cycloalkenylsulfonyl, $(C_3-C_8)$-halocycloalkylsulfonyl, $(C_4-C_8)$-halocycloalkenylsulfonyl, $(C_3-C_8)$-cycloalkyl-$(C_1-C_4)$-alkylsulfonyl, $(C_4-C_8)$-cycloalkenyl-$(C_1-C_4)$-alkylsulfonyl, $(C_3-C_8)$-cycloalkylsulfinyl, $(C_1-C_6)$-alkylsulfonyl, $(C_1-C_6)$-haloalkylsulfonyl, $(C_3-C_8)$-cycloalkylsulfonyl, $(C_1-C_6)$-dialkylamino, $(C_1-C_6)$-alkylamino, $(C_3-C_8)$-cycloalkylamino, $(C_1-C_6)$-trialkylsilyl, aryl, aryloxy, arylthio, aryl-$(C_1-C_4)$-alkyl, arylamino, aryl-$(C_1-C_4)$-alkoxy, where the cyclic moiety of the six last-mentioned radicals is unsubstituted or substituted by one or more radicals selected from the group consisting of halogen, nitro, $(C_1-C_4)$-alkyl, $(C_1-C_4)$-haloalkyl, $(C_1-C_4)$-alkoxy and $(C_1-C_4)$-haloalkoxy, and if $R^9$ is aryl or heterocyclyl, $(C_1-C_4)$-alkyl or $C_1-C_4$)-haloalkyl.

Among the radicals $R^5$, particular preference is given to phenyl radicals which are unsubstituted or mono- or polysubstituted; in particular to those of the formula (IIa).

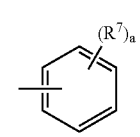

(IIa)

where the symbols and indices are as defined below:

$R^7$ has the meanings given above;

a is a, 1, 2, 3 or 4, preferably 0, 1 or 2.

The term "halogen" includes fluorine, chlorine, bromine and iodine. Preferred are chlorine or fluorine.

The term "—S(halogen)$_5$" includes the groups —SI$_5$, —SBr$_5$, —SCl$_5$ and in particular —SF$_5$.

The term "(C$_1$–C$_6$)-alkyl" is to be understood as meaning an unbranched or branched hydrocarbon radical having one to six carbon atoms, such as, for example, the methyl, ethyl, propyl, isopropyl, 1-butyl, 2-butyl, 2-methylpropyl, tert-butyl, 1-pentyl, 2-methylbutyl, 1,1dimethylpropyl or 1-hexyl radical. Correspondingly, an alkyl radical having a larger range of carbon atoms is to be understood as meaning an unbranched or branched saturated hydrocarbon radical which contains a number of carbon atoms which corresponds to the stated range. Accordingly, the term "(C$_1$–C$_{10}$)-alkyl" includes the abovementioned alkyl radicals and also, for example, the heptyl, octyl, 2-ethylhexyl, nonyl or decyl radical.

"(C$_1$–C$_6$)-Haloalkyl" is to be understood as meaning an alkyl group mentioned under the expression "(C$_1$–C$_6$)-alkyl" in which one or more hydrogen atoms are replaced by the same number of identical or different halogen atoms, preferably by chlorine or fluorine, such as the trifluoromethyl, the 1-fluoroethyl, the 2,2,2-trifluoroethyl, the chloromethyl, the fluoromethyl, the difluoromethyl and the 1,1,2,2-tetrafluoroethyl group.

"(C$_1$–C$_6$)-Alkoxy" is to be understood as meaning an alkoxy group whose hydrocarbon radical has the meaning given under the term "(C$_1$–C$_6$)-alkyl". Alkoxy groups having a larger range of carbon atoms are to be understood accordingly.

The terms "alkenyl" and "alkynyl" with a range of carbon atoms stated as prefix denote a straight-chain or branched hydrocarbon radical having a number of carbon atoms which corresponds to this stated range and which contains at least one multiple bond which can be located in any position of the respective unsaturated radical. "(C$_2$–C$_4$)-Alkenyl" accordingly denotes, for example, the vinyl, allyl, 2-methyl-2-propenyl or 2-butenyl group; "(C$_2$–C$_6$)-alkenyl" denotes the abovementioned radicals and also, for example, the pentenyl, 2-methylpentenyl or the hexenyl group. "(C$_2$–C$_4$)-Alkynyl" denotes, for example, the ethynyl, propargyl, 2-methyl-2-propynyl or 2-butynyl group. "(C$_2$–C$_6$)-Alkynyl" is to be understood as meaning the abovementioned radicals and also, for example, the 2-pentynyl or the 2-hexynyl group, and "(C$_2$–C$_{10}$)-alkynyl" is to be understood as meaning the abovementioned radicals and also, for example, the 2-octynyl or the 2-decynyl group.

"(C$_3$–C$_8$)-Cycloalkyl" denotes monocyclic alkyl radicals, such as the cyclopropyl, cyclobutyl, cyclopentyl, cyclohexyl, cycloheptyl or cyclooctyl radical, and denotes bicyclic alkyl radicals, such as the norbornyl radical.

The expression "(C$_3$–C$_8$)-cycloalkyl-(C$_1$–C$_4$)-alkyl" is to be understood as meaning, for example, the cyclopropylmethyl, cyclopentylmethyl, cyclohexylmethyl, cyclohexylethyl and cyclohexylbutyl radical, and the expression "(C$_1$–C$_6$)-alkyl-(C$_3$–C$_8$)-cycloalkyl" is to be understood as meaning, for example, the 1-methylcyclopropyl, 1-methylcyclopentyl, 1-methylcyclohexyl, 3-hexylcyclobutyl and the 4-tert-butylcyclohexyl radical.

"(C$_1$–C$_4$)-Alkoxy-(C$_1$–C$_6$)-alkyloxy" denotes an alkoxy group as defined above which is substituted by a further alkoxy group, such as, for example, 1-ethoxyethoxy.

"(C$_3$–C$_8$)-Cycloalkoxy" or "(C$_3$–C$_8$)-cycloalkylthio" is to be understood as meaning one of the abovementioned (C$_3$–C$_8$)-cycloalkyl radicals which is attached via an oxygen or sulfur atom.

"(C$_3$–C$_8$)-Cycloalkyl-(C$_1$–C$_6$)-alkoxy" denotes, for example, the cyclopropylmethoxy, cyclobutylmethoxy, cyclopentylmethoxy, cyclohexylmethoxy, cyclohexylethoxy or the cyclohexylbutoxy group.

The expression "(C$_1$–C$_4$)-alkyl-(C$_3$–C$_8$)-cycloalkoxy" denotes, for example, the methylcyclopropyloxy, methylcyclobutyloxy or the butylcyclohexyloxy group.

"(C$_1$–C$_6$)-Alkylthio" denotes an alkylthio group whose hydrocarbon radical has the meaning given under the expression "(C$_1$–C$_6$)-alkyl".

Similarly, "(C$_1$–C$_6$)-alkylsulfinyl" denotes, for example, the methyl-, ethyl-, propyl-, isopropyl-, butyl-, isobutyl-, sec-butyl- or tert-butylsulfinyl group and "(C$_1$–C$_6$)-alkylsulfonyl" denotes, for example, the methyl-, ethyl-, propyl-, isopropyl-, butyl-, isobutyl-, sec-butyl- or tert-butylsulfonyl group.

"(C$_1$–C$_6$)-Alkylamino" denotes a nitrogen atom which is substituted by one or two identical or different alkyl radicals of the above definition.

The expression "(C$_1$–C$_6$)-mono- or -dialkylcarbamoyl" denotes a carbamoyl group having one or two hydrocarbon radicals which have the meaning given under the expression "(C$_1$–C$_6$)-alkyl" and which, in the case of two hydrocarbon radicals, can be identical or different.

Similarly, "(C$_1$–C$_6$)-dihaloalkylcarbamoyl" denotes a carbamoyl group which carries two (C$_1$–C$_6$)-haloalkyl radicals according to the above definition or one (C$_1$–C$_6$)-haloalkyl radical and one (C$_1$–C$_6$)-alkyl radical according to the above definition.

"(C$_1$–C$_6$)-Alkanoyl" denotes, for example, the formyl, acetyl, propionyl, butyryl or 2-methylbutyryl group.

The expression "aryl" is to be understood as meaning a carbocyclic, i.e. constructed of carbon atoms, aromatic radical having preferably 6 to 14, in particular 6 to 12, carbon atoms, such as, for example, phenyl, naphthyl or biphenylyl, preferably phenyl.

"Aroyl" accordingly denotes an aryl radical as defined above which is attached via a carbonyl group, such as, for example, the benzoyl group.

The expression "heterocyclyl" preferably denotes a cyclic radical which can be completely saturated, partially unsaturated or completely unsaturated or aromatic and which can be interrupted by at least one or more identical or different atoms selected from the group consisting of nitrogen, sulfur and oxygen, where, however, two oxygen atoms may not be directly adjacent and at least one carbon atom has to be present in the ring, such as, for example, a thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine, 4H-quinolizine, piperidine, pyrrolidine, oxazoline, tetrahydrofuran, tetrahydropyran, isoxazolidine or thiazolidine radical. Accordingly, the expression "heteroaromatic" embraces, from among the meanings mentioned above under "heterocyclyl", in each case the completely unsaturated aromatic heterocyclic compounds.

Heterocyclyl particularly preferably denotes a saturated, partially saturated or aromatic ring system having 3 to 6 ring members and 1 to 4 heteroatoms selected from the group consisting of O, S and N, where at least one carbon atom has to be present in the ring.

Very particularly preferably, heterocyclyl denotes a pyridine, pyrimidine, (1,2,4)-oxadiazole, (1,3,4)-oxadiazole, pyrrole, furan, thiophene, oxazole, thiazole, imidazole, pyrazole, isoxazole, 1,2,4-triazole, tetrazole, pyrazine, pyridazine, oxazoline, thiazoline, tetrahydrofuran, tetrahydropyran, morpholine, piperidine, piperazine, pyrroline, pyrrolidine, oxazolidine, thiazolidine, oxirane and oxetane. radical.

"Aryl-$(C_1$–$C_4)$-alkoxy" denotes an aryl radical which is attached via a $(C_1$–$C_4)$-alkoxy group, for example the benzyloxy, phenylethoxy, phenylbutoxy or naphthylmethoxy radical.

"Arylthio" denotes an aryl radical which is attached via a sulfur atom, for example the phenylthio or the 1- or 2-naphthylthio radical. Similarly, "aryloxy" denotes, for example, the phenoxy or 1- or 2-naphthyloxy radical.

"Aryl-$(C_1$–$C_4)$-alkylthio" denotes an aryl radical which is attached via an alkylthio radical, for example the benzylthio, naphthylmethylthio or the phenylethylthio radical.

The expression "$(C_1$–$C_6)$-trialkylsilyl" denotes a silicon atom which carries three identical or different alkyl radicals according to the above definition. Similarly, "aryl-$(C_1$–$C_6)$-dialkylsilyl" denotes a silicon atom which carries one aryl radical and two identical or different alkyl radicals according to the above definition, "diaryl-$(C_1$–$C_6)$-alkylsilyl" denotes a silicon atom which carries one alkyl radical and two identical or different aryl radicals according to the above definition and "triarylsilyl" denotes a silicon atom which carries three identical or different aryl radicals according to the above definition.

The substituents on the various aliphatic, aromatic and heterocyclic ring systems preferably include halogen, nitro, cyano, di-$(C_1$–$C_4)$-alkylamino, $(C_1$–$C_4)$-alkyl, $(C_1$–$C_4)$-trialkylsilyl, $(C_1$–$C_4)$-alkoxy, $(C_1$–$C_4)$-alkoxy-$(C_1$–$C_4)$-alkyl, $(C_1$–$C_2)$-alkoxy-$[CH_2CH_2]_{1,2}$-ethoxy, $(C_1$–$C_4)$-alkylthio, $(C_1$–$C_4)$-alkylsulfinyl, $(C_1$–$C_4)$-alkylsulfonyl, phenyl, benzyl, phenoxy, phenylthio, halophenoxy, $(C_1$–$C_4)$-alkylthiophenoxy, $(C_1$–$C_4)$-alkoxyphenoxy, phenylthio, heterocyclyl, heterocyclylthio, heterocyclyloxy, haloheterocyclyloxy, alkylheterocyclyloxy or alkoxyheterocyclyloxy, where in the alkyl radicals and the radicals derived therefrom one or more hydrogen atoms, in the case of fluorine also up to the maximum number, may be replaced by halogen, preferably by chlorine or fluorine.

Particularly preferred substituents are, in particular for cyclic systems, halogen, cyano, nitro, amino, hydroxyl, thio, $(C_1$–$C_4)$-alkyl, $(C_1$–$C_4)$-haloalkyl, $(C_3$–$C_8)$-cycloalkyl, $(C_1$–$C_4)$-alkoxy, $(C_1$–$C_4)$-haloalkoxy, $(C_1$–$C_4)$-alkylthio, $(C_1$–$C_4)$-haloalkylthio, $(C_1$–$C_4)$-alkylamino, $(C_1$–$C_4)$-haloalkylamino, formyl and $(C_1$–$C_4)$-alkanoyl.

Depending on the nature of the substituents defined above, the compounds of the formulae (I) and (II) have acidic or basic properties and are capable of forming salts. If, for example, the compounds of the formulae (I) and (II) carry groups such as hydroxyl, carboxyl or other groups which induce acidic properties, these compounds can be reacted with bases to form salts. Suitable bases are, for example, hydroxides, carbonates and bicarbonates of the alkali metals and alkaline earth metals, in particular those of sodium, potassium, magnesium and calcium, furthermore ammonia, primary, secondary and tertiary amines with $(C_1$–$C_4)$-alkyl radicals and mono-, di- and trialkanolamines of $(C_1$–$C_4)$-alkanols. If, for example, the compounds of the formulae (I) and (II) carry groups such as amino, alkylamino or other groups which induce basic properties, these compounds can be reacted with acids to form salts. Suitable acids are, for example, mineral acids, such as hydrochloric, sulfuric and phosphoric acid, organic acids, such as acetic acid or oxalic acid, and acidic salts, such as $NaHSO_4$ and $KHSO_4$. The salts obtainable in this manner likewise have insecticidal, acaricidal and miticidal properties.

The compounds of the formulae (I) and (II) can have an asymmetrically substituted sulfur atom and/or one or more asymmetrically substituted carbon atoms or stereoisomers on double bonds. Therefore, it is possible for enantiomers or diastereomers to be present. The invention embraces both the pure isomers and their mixtures. The mixtures of diastereomers can be separated into the isomers by customary methods, for example by selective crystallization from suitable solvents or by chromatography. Racemates can be separated into the enantiomers by customary methods.

The preparation of the compounds according to the invention is carried out by methods known per se from the literature, as described in standard works on organic synthesis (cf., for example, T. L. Gilchrist, C. J. Moody, Chem. Rev. 77, 409 (1977); Houben-Weyl, Methoden der Organischen Chemie [Methods of Organic Chemistry], Vol. E11, p. 877).

The preparation is carried out under reaction conditions which are known and suitable for the reactions mentioned. It is also possible to use variants which are known per se but not mentioned here in detail.

If desired, the starting materials can also be formed in situ, i.e. they are not isolated from the reaction mixture but immediately reacted further to give the compounds of the formulae (I) and (II).

The present invention also relates to processes for preparing compounds of the formulae (I) and (II).

Compounds of the formula (I) can be obtained by reacting thiols with nitrene-forming compounds such as N-chloroamides or azides. The nitrene-forming compound can also be synthesized in the solution. However, the reaction can also be carried out in an inverted manner using halomercaptan and amide. Typical solvents are organic solvents which are inert under the reaction conditions and which may not be protic, for example toluene or acetonitrile. Typically, bases are added to the reaction solution; however, it is also possible to use the pre-formed salt.

To prepare compounds of the formula (I) in which $R^1$, $R^2$, $R^3$, $R^4$, $R^5$, Y, n and X have the meanings given for formula (I) and m is 0, a carboxamide of the formula (III) in which $R^1$, $R^2$, $R^3$, $R^4$, Y, n and X have the meanings given in formula (I) is, for example, reacted with a halogenating agent, preferably a chlorinating or brominating agent, to give a compound of the formula (IV) in which $R^1$, $R^2$, $R^3$, $R^4$, Y, n and X have the meanings given for formula (I) and Hal is halogen, preferably chlorine or bromine, and this compound is then reacted with a thioether $R^5SH$, in which $R^5$ has the meanings given for formula (I), in the presence of a base to give the end products of the formula (I):

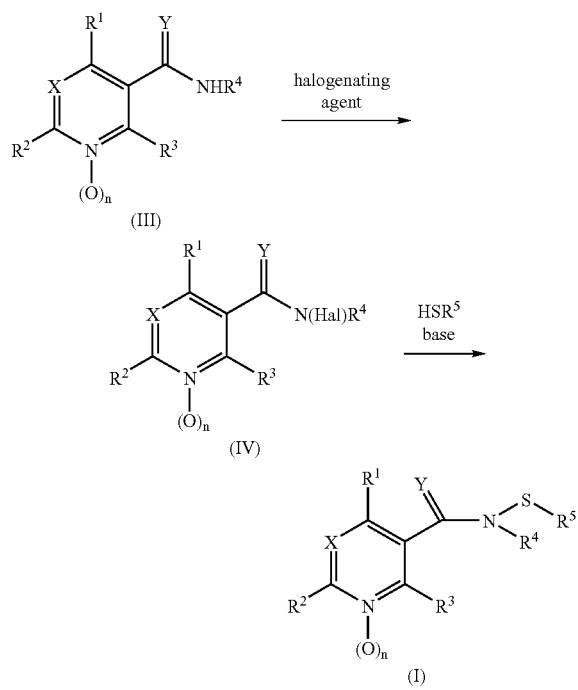

(III)

(IV)

(I)

Halogenating agents suitable for preparing the compounds (IV) are, for example, organo- or alkali metal hypochlorites, such as, for example, tert-butyl hypochlorite or sodium hypochlorite or potassium hypochlorite, alkali metal hypobromites, such as sodium hypobromite or potassium hypobromite, or the elemental halogens in the presence of a base such as, for example, alkali metal hydroxide or carbonate or alkaline earth metal hydroxide or carbonate.

N-Chloro-4-trifluoromethylnicotinamide and its salts of the formula (IVa).

(IVa)

in which A is a non-oxidizable organic or inorganic anion can be prepared by chlorinating 4-trifluoromethylnicotinamide with $Cl_2$ in aqueous acid and, if desired, subsequent anion exchange and/or, if desired, reaction with a base to give N-chloro-4-trifluoromethylnicotinamide.

In the context of this description, "non-oxidizable" means that the corresponding anion does not react with the N—Cl group of the N-chloro-4-trifluoromethylnicotinamide. A is preferably F, $HF_2$, Cl, $BF_4$, $PF_6$, $HSO_4$, ½ $SO_4$, $CH_3COO$, $CF_3COO$, $CF_3SO_3$, $CH_3SO_3$, p-$CH_3$—$C_6H_5SO_3$ or $H_2PO_4$.

The starting material 4-trifluoromethylnicotinamide and its N-substituted analogs are known and, together with their preparation, described, for example, in EP-A 0580374 and DE-A 100 619 67.

The reaction temperature is usually from −5° C. to +40° C., preferably from 0° C. to +25° C.

The process is carried out in an aqueous acid, for example HCl, $H_2SO_4$, $HBF_4$, $CH_3COOH$ or $CF_3COOH$, preferably HCl (preferred concentration 3–10% by weight). It is also possible to use mixtures of a plurality of acids.

$Cl_2$ is preferably employed in gaseous form; in general in amounts of from 1 to 1.5 mol, in particular from 1 to 1.3 mol, preferably from 1 to 1.2 mol, based on 1 mol of 4-trifluoromethylnicotinamide.

Chlorination of 4-trifluoromethylnicotinamide gives the corresponding salt, preferably the hydrochloride.

Work-up is carried out by methods known to the person skilled in the art; for example, the precipitated product is filtered off, washed and dried.

A subsequent anion exchange can be carried out by known methods familiar to the person skilled in the art. The salt obtained in the reaction can be dissolved, for example, in a suitable solvent in which the salt desired later on is insoluble. Reaction with a salt which contains the desired anion and is likewise soluble in this solvent gives, by precipitation, the desired salt, since this is insoluble in the chosen solvent.

If desired, the free N-chloro compound can be released by reaction with a base in a simple manner familiar to the person skilled in the art.

Suitable bases are, for example, hydroxides, carbonates, bicarbonates, acetates of the alkali metals and alkaline earth metals, in particular those of sodium, potassium, magnesium and calcium, furthermore tertiary amines having ($C_1$–$C_4$)-alkyl radicals. It is furthermore possible to isolate the free base by treatment with water and extraction with organic solvents.

The reaction of the N-haloamides (IV), optionally also as salt, to give the end products (I) is carried out, for example, in an inert solvent such as, for example, dichloromethane, chloroform, carbon tetrachloride or benzene, in a temperature range between 0° C. and 100° C., preferably between 20° C. and 50° C. and in the presence of a base.

Suitable bases are, for example, alkali metal or alkaline earth metal hydroxides, carbonates or bicarbonates or organic bases, such as, for example, trialkylamines or pyridine.

The reaction sequence described above can, if appropriate, also be carried out as a one-pot reaction, it also being possible for intermediates of the formula (V) in which $R^5$ is as defined above under formula (I) and Z is a halogen radical, preferably chlorine or bromine, to occur as reaction partners of the amide (III).

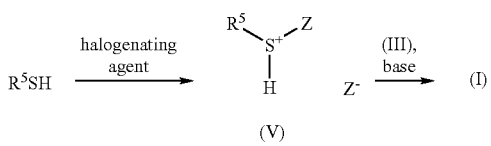

(V)

Compounds of the formula (I), in which $R^1$, $R^2$, $R^3$, $R^4$, $R^5$, Y, n, m and X are as defined under formula (I), can furthermore be prepared by reacting a carboxylic acid or thiocarboxylic acid of the formula (VI)

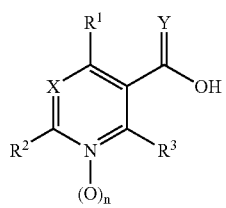

(VI)

in which $R^1$, $R^2$, $R^3$, Y, X and n are as defined under formula (I) in the form of an activated derivative of this acid in the presence of a base with a compound of the formula (VII), in which $R^4$, $R^5$ and m are as defined under formula (I)

(VII)

Suitable activated derivatives of the acid which may be used are, for example, anhydrides, azolides or, preferably, acid chlorides. Suitable bases are, for example, amines, such as triethylamine, diisopropylethylamine, pyridine or lutidine or else alkali metal or alkaline earth metal hydroxides, carbonates or bicarbonates. The reaction is advantageously carried out in an inert solvent, such as, for example, dichloromethane, chloroform, carbon tetrachloride, benzene, toluene, diethyl ether or tetrahydrofuran, or else in mixtures of these solvents, in a temperature range between 0° C. and 100° C., preferably between 20° C. and 50° C.

Compounds of the formula (Ia) in which m=0, $R^4$ is hydrogen and $R^5$ is one of the groups defined above and has a β-hydrogen atom, preferably a branched alkyl group having a β-hydrogen atom, can also be prepared by thermal decomposition of the corresponding sulfimides (VIII), according to the scheme below:

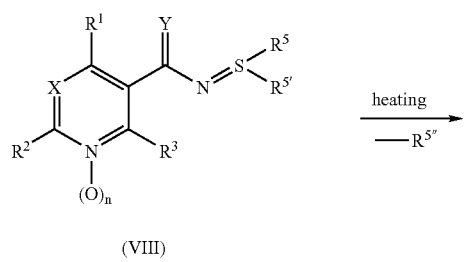

(VIII)

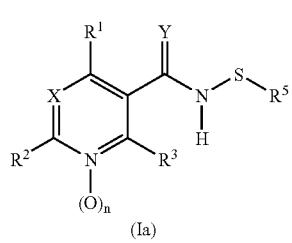

(Ia)

Here, the radicals $R^1$, $R^2$, $R^3$, $R^5$, X and Y and the index n are as defined above, $R^{5'}$ has, independently of $R^5$, one of the meanings given for $R^5$, and $R^{5''}$ is the ethylenically unsaturated leaving group derived from $R^{5'}$ whose number of hydrogen atoms is reduced by one. In addition to symmetrically substituted compounds of the formula VIII ($R^5=R^{5'}$), it is also possible to use asymmetrically substituted compounds ($R^5 \neq R^{5'}$).

The reaction can be carried out using the undiluted substance of the formula (VIII), at temperatures above its melting point. However, it is also possible to carry out the reaction in aprotic organic solvents. Thus, for example, S,S-2-butyl-N-(4-trifluoromethyl)nicotinoylsulfimide can be converted into N-2-butylthio-4-trifluoromethylnicotinamide by heating at 100° C. for 5 hours. Work-up can be carried out by standard processes, for example by chromatographic processes.

It is also possible to invert this reaction to provide sulfimides of the formula (VIII). Accordingly, the invention also relates to a process for preparing compounds of the formula (VIII) by converting compounds of the formula (Ia). To produce sulfimides of the formula (VIII) in which $R^1$, $R^2$, $R^3$, $R^5$, Y, n and X have the meanings given above for formula (I), a compound of the formula (Ia) in which $R^1$, $R^2$, $R^3$, $R^5$, Y, n and X have the meanings given above is reacted in the presence of a compound $R^{5'}$-Z, in which $R^{5'}$ is as defined above and Z is a leaving group, and a base according to the scheme below:

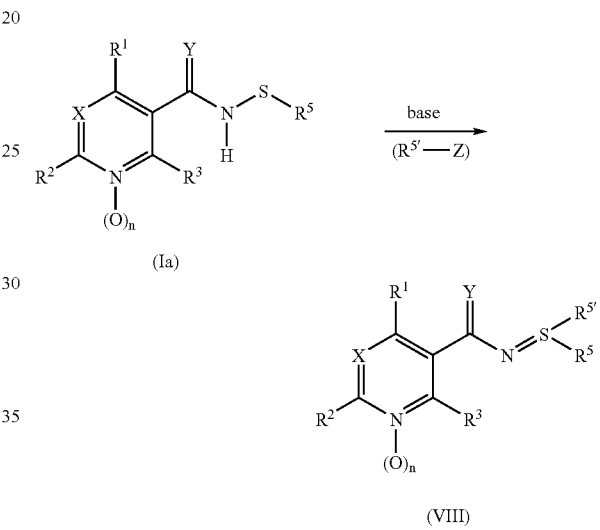

(VIII)

Typical leaving groups Z are halogen, mesylate and tosylate.

In addition to symmetrically substituted compounds of the formula (VIII) ($R^5=R^{5'}$), this process also provides, in particular, the asymmetrically substituted compounds of the formula (VIII) ($R^5 \neq R^{5'}$).

The process according to the invention is preferably suitable for carrying out the reactions in parallel.

The precursors of the formula (VIII) for the synthesis of the compounds of the formula (I) can be obtained, for example, by reacting a carboxylic acid or thiocarboxylic acid of the formula (VI)

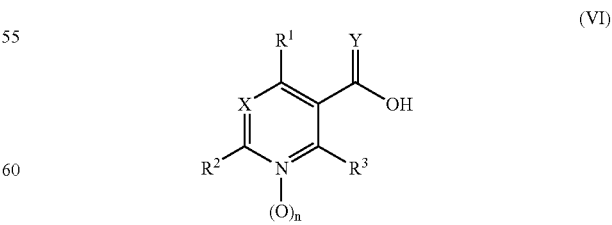

(VI)

in which $R^1$, $R^2$, $R^3$, X, Y and n have the meanings given for formula (I) in the form of an activated derivative of this acid in the presence of a base with a compound of the formula (IX), preferably as a salt,

in which R⁵ has the meanings given for formula (I).

Derivatization of the compounds of the formula (Ib) into compounds of the formula (II) having radicals R⁴' which are not hydrogen by the Mitsunobu reaction is carried out according to the scheme below:

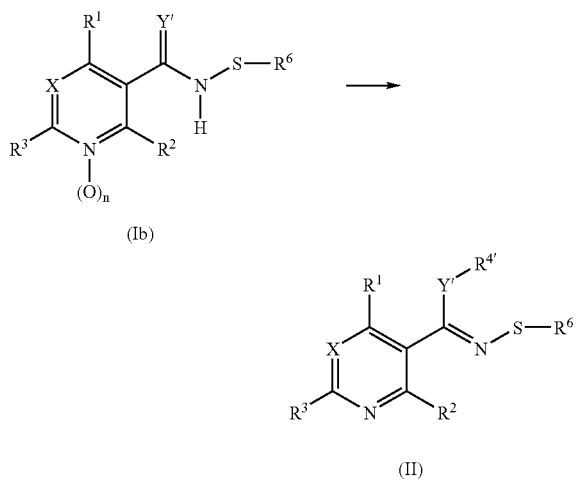

This gives the O— or S-derivatized products of the formula (II) in addition to the N-derivatized products of the formula (I) as byproduct.

The reaction is carried out under Mitsunobu conditions, i.e. by reacting the NH derivative With an alcohol, R⁴'—OH (e.g. butanol), in the presence of an azodicarboxylic acid diester and a phosphine.

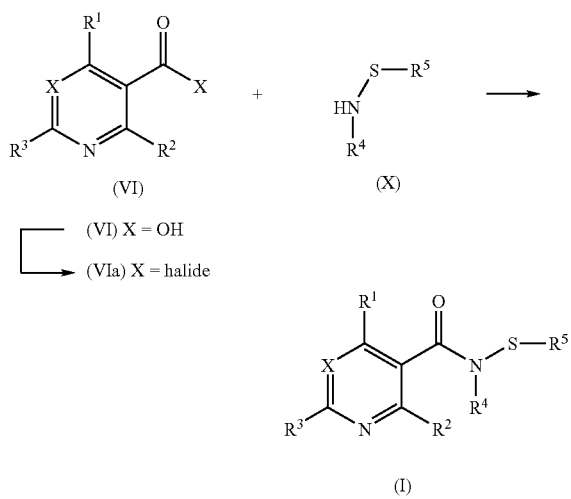

The acid (VI X═OH) can be activated by conversion into the acid halide (VIa, X=halide). Possible halogenating agents include oxalyl chloride, POCl₃, PCl₃, PCl₅, SOCl₂ or SO₂Cl₂. The resulting acid halides can then be reacted further with thioamines (X). Typically, the acid halide (VIa, X=halide) is reacted with thioamines in the presence of a base. Suitable bases are, for example, alkali metal hydroxides, carbonates or bicarbonates or alkaline earth metal hydroxides, carbonates or bicarbonates or organic bases, such as, for example, trialkylamines or pyridines. It is also possible to use bases which are attached to a solid phase, such as, for example, S-trisamine from Agilent or Polystyrene AM NH2 from Rapp. Advantageously, the reaction is carried out in an inert solvent, such as, for example, dichloromethane, chloroform, carbon tetrachloride, benzene, toluene, diethyl ether or tetrahydrofuran, or else in mixtures of these solvents in a temperature range between 0° C. and 100° C., preferably between 20° C. and 50° C.

Alternatively, the acid can also be reacted directly with thioamine derivatives using coupling reagents such as CDI, DCC or EDAC.

To produce compounds of the formulae (I) and (II) in which n is 1, it is possible to oxidize the pyridine nitrogen, preferably before introducing the R⁵S group (see, for example, Houben-Weyl, Methoden der Organischen Chemie, Vol. E 7b, part 2, p. 565, G. Thieme Verlag, Stuttgart 1992). Suitable oxidizing agents are, for example, organic peracids, such as 3-chloroperbenzoic acid, and H₂O₂.

If desired, the compounds of the formulae (I) and (II) prepared by the above processes can, if m is 0, be oxidized at the sulfur to give the compounds of the formulae (I) and (II) in which m is 1 or 2 (see, for example, Houben-Weyl, Methoden der Organischen Chemie, Vol. E11, p. 1299 ff., G. Thieme Verlag, Stuttgart 1985). Suitable oxidizing agents are, for example, sodium periodate or organic peracids, such as 3-chloroperbenzoic acid.

Furthermore, if appropriate, compounds of the formulae (I) and (II) in which R² and/or R³ are a halogen atom, preferably chlorine or fluorine, can be converted by reaction with alcohols, thiols or primary or secondary amines in the presence of a base to other compounds of the formulae (I) and (II) in which the radical R² and/or R³ denotes an alkoxy, alkylthio or amino group.

Further references concerning preparation of the compounds according to the invention and the various starting materials can be found in standard works on organic synthesis, such as, for example: T. L. Gilchrist, C. J. Moody, Chem. Rev. 77, 409 (1977) or Houben-Weyl, Methoden der Organischen Chemie, Vol. E11, p. 877.

Collections of compounds of the formulae (I) and (II) which can be synthesized by the abovementioned scheme may also be prepared in a parallel manner, and this may be effected manually or in a semiautomated or fully automated manner. In this case, it is possible, for example, to automate the procedure of the reaction, work-up or purification of the products or of the intermediates. In total, this is to be understood as meaning a procedure as is described, for example, by S. H. DeWitt in "Annual Reports in Combinatorial Chemistry and Molecular Diversity: Automated Synthesis", Volume 1, Verlag Escom 1997, pages 69 to 77.

A series of commercially available apparatuses as are offered by, for example, Stem Corporation, Woodrolfe Road, Tollesbury, Essex, CM9 8SE, England or H+P Labortechnik GmbH, Bruckmannring 28, 85764 Oberschleißheim, Germany or Radleys, Shirehill, Saffron Walden, Essex, England maybe used for the parallel procedure of the reaction and work-up. For the parallel purification of compounds of the formula (I), or of intermediates obtained during the preparation, use may be made, inter alia, of chromatography apparatuses, for example those from ISCO, Inc., 4700 Superior Street, Lincoln, Nebr. 68504, USA.

The apparatuses mentioned lead to a modular procedure in which the individual process steps are automated, but manual operations must be performed between the process steps. This can be prevented by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to the methods described here, compounds of the formulae (I) and (II) may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example. Barry A. Bunin in "The Combinatorial Index", Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131–5135), in which products from IRORI, 11149 North Torrey Pines Road, La Jolla, Calif. 92037, USA are employed, may be semi automated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation by the processes described herein yields compounds of the formulae (I) and (II) in the form of substance collections which are termed libraries.

The present invention also relates to libraries which comprise at least two compounds of the formulae (I) and (II).

The compounds of the formulae (I) and (II) are suitable for controlling animal pests, in particular insects, arachnids, helminths and mollusks, very especially preferably for controlling insects and arachnids which are encountered in agriculture, in livestock breeding, in forests, in the protection of stored goods and materials, and in the hygiene sector, and have good plant tolerance and favorable toxicity to warm-blooded species. They are active against normally sensitive and resistant species and against all or individual developmental stages. The abovementioned pests include:

From the order of the *Acarina*, for example, *Acarus siro*, *Argas* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa*, *Panonychus* spp., *Tetranychus* spp., *Eotetranychus* spp., *Oligonychus* spp., *Eutetranychus* spp.

From the order of the *Isopoda*, for example, *Oniscus aselus*, *Armadium vulgare*, *Porcellio scaber*.

From the order of the *Diplopoda*, for example, *Blaniulus guttulatus*.

From the order of the *Chilopoda*, for example, *Geophilus carpophagus, Scutigera* spp.

From the order of the *Symphyla*, for example, *Scutigerella immaculata*.

From the order of the *Thysanura*, for example, *Lepisma saccharina*.

From the order of the *Collembola*, for example, *Onychiurus armatus*.

From the order of the *Orthoptera*, for example, *Blatta orientalis, Periplaneta americana, Leucophaea maderae, Blattella germanica, Acheta domesticus, Gryllotalpa* spp., *Locusta migratoria migratorioides, Melanoplus differentialis, Schistocerca gregaria*.

From the order of the *Isoptera*, for example, *Reticulitermes* spp.

From the order of the *Anoplura*, for example, *Phylloera vastatrix, Pemphigus* spp., *Pediculus humanus corporis, Haematopinus* spp., *Linognathus* spp.

From the order of the *Mallophaga*, for example, *Trichodectes* pp., *Damalinea* spp.

From the order of the *Thysanoptera*, for example, *Hercinothrips femoralis, Thrips tabaci*.

From the order of the *Heteroptera*, for example, *Eurygaster* spp., *Dysdercus intermedius, Piesma quadrata, Cimex lectularius, Rhodnius prolixus, Triatoma* spp.

From the order of the *Homoptera*, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelus bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the *Lepidoptera*, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana*.

From the order of the *Coleoptera*, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylloides chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrynchus assimilis, Hypera postica, Dermestes* spp., *Trogoderma, Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica*.

From the order of the *Hymenoptera*, for example, *Diprion* spp., *Hoplocampa* spp., *Lasius* spp., *Monomorium pharaonis, Vespa* spp.

From the order of the *Diptera*, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hypobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa*.

From the order of the *Siphonaptera*, for example, *Xenopsylla cheopsis, Ceratophyllus* spp.

From the order of the *Arachnida*, for example, *Scorpio maurus, Latrodectus mactans*.

From the class of the *helminths*, for example, *Haemonchus, Trichostrongulus, Ostertagia, Cooperia, Chabertia, Strongyloides, Oesophagostomum, Hyostrongulus, Ancylostoma, Ascaris* and *Heterakis* and also *Fasciola*.

From the class of the *Gastropoda*, for example, *Deroceras* spp., *Arion* spp., *Lymnaea* spp., *Galba* spp., *Succinea* spp., *Biomphalaria* spp., *Bulinus* spp., *Oncomelania* spp.

From the class of the *Bivalva*, for example, *Dreissena* spp. Furthermore protozoa, such as *Eimeria*, can be controlled.

The plant-parasitic nematodes which can be controlled in accordance with the invention include, for example, the root-parasitic soil-dwelling nematodes such as, for example, those of the genera *Meloidogyne* (root knot nematodes, such as *Meloidogyne incognita, Meloidogyne hapla* and *Meloidogyne javanica*), *Heterodera* and *Globodera* (cyst-forming nematodes, such as *Globodera rostochiensis, Globodera pallida, Heterodera trifolii*) and of the genera *Radopholus*, such as *Radopholus similis, Pratylenchus* such as *Pratylenchus neglectus, Pratylenchus penetrans* and *Pratylenchus curvitatus;*

*Tylenchulus* such as *Tylenchulus semipenetrans, Tylenchorhynchus*, such as *Tylenchorhynchus dubius* and *Tylenchorhynchus claytoni, Rotylenchus* such as *Rotylenchus robustus, Heliocotylenchus* such as *Haliocotylenchus multicinctus, Belonoaimus* such as *Belonoaimus longicaudatus, Longidorus* such as *Longidorus elongatus, Trichodorus* such as *Trichodorus primitivus* and *Xiphinema* such as *Xiphinema index*.

Other nematode genera which can be controlled using the compounds according to the invention are *Ditylenchus* (stem parasites, such as *Ditylenchus dipsaci* and *Ditylenchus destructor*), *Aphelenchoides* (foliar nematodes, such as *Aphelenchoides ritzemabosi*) and *Anguina* (seed nematodes, such as *Anguina tritici*).

The invention also relates to compositions, for example crop protection compositions, preferably insecticidal, acaricidal, ixodicidal, nematicidal, molluscicidal or fungicidal, especially preferably insecticidal and acaricidal, compositions which comprise one or more compounds of the formulae (I) and/or (II) in addition to suitable formulation auxiliaries.

In general, the compositions according to the invention comprise 1 to 95% by weight of the active substances of the formulae (I) and/or (II).

To prepare the compositions according to the invention, the active substance and the other additives are combined and brought into a suitable use form.

The invention also relates to compositions, in particular insecticidal and acaricidal compositions, which comprise the compounds of the formulae (I) and/or (II) in addition to suitable formulation auxiliaries.

In general, the compositions according to the invention comprise 1 to 95% by weight of the active substances of the formulae (I) and/or (II). They can be formulated in various ways, depending on the biological and/or chemical-physical parameters which prevail. The following are examples of possible formulations:

Wettable powders (WP), emulsifiable concentrates (EC), aqueous solutions (SL), emulsions, sprayable solutions, oil- or water-based dispersions (SC), suspoemulsions (SE), dusts (DP), seed-dressing products, granules in the form of microgranules, spray granules, coated granules and adsorption granules, water-dispersible granules (WG), ULV formulations, microcapsules, waxes or baits.

These individual types of formulations are known in principle and are described, for example, in: Winnacker-Küchler, "Chemische Technologie" [Chemical Technology], Volume 7, C. Hanser Verlag Munich, 4th Edition 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The necessary formulation auxiliaries, i.e. carrier materials and/or surface-active substances such as inert materials, surfactants, solvents and other additives, are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's, "Detergents and A Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1967; Winnacker-Küchler, "Chemische Technologie", Volume 7, C. Hanser Verlag Munich, 4th Edition 1986.

Based on these formulations, it is also possible to prepare combinations with other pesticidally active materials, fertilizers and/or growth regulators, for example in the form of a ready-mix formulation or a tank mix. Wettable powders are preparations which are uniformly dispersible in water which, besides the active substance, also comprise wetters, for example polyoxyethylated alkylphenols, polyoxyethylated fatty alcohols, alkylsulfonates or alkylphenolsulfonates and dispersants, for example sodium lignosulfonate or sodium 2,2'-dinaphthylmethane-6,6'-disulfonate, in addition to a diluent or inert material.

Emulsifiable concentrates are prepared by dissolving the active substance in an organic solvent, for example butanol, cyclohexanone, dimethylformamide, xylene or else higher-boiling aromatics or hydrocarbons, with addition of one or more emulsifiers. As emulsifiers, the following can be used, for example: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propyleneoxide/ethylene oxide condensates, alkyl polyethers, sorbitan fatty acid esters, polyoxyethylene sorbitan fatty acid esters or polyoxyethylene sorbitol esters.

Dusts are obtained, for example, by grinding the active substance with finely divided solid materials, for example talc or natural clays, such as kaolin, bentonite, pyrophyllite or diatomaceous earth. Granules can be prepared either by atomizing the active substance onto adsorptive, granulated inert material or by applying active substance concentrates onto the surface of carrier materials such as sand or kaolinites, or of granulated inert material, by means of adhesives, for example polyvinyl alcohol or sodium polyacrylate, or else mineral oils. Suitable active substances can also be granulated in the manner which is customary for the preparation of fertilizer granules, if desired as a mixture with fertilizers.

The active substance concentration in wettable powders is usually approximately 10 to 90% by weight, the remainder to 100% by weight is composed of customary formulation constituents. In the case of emulsifiable concentrates, the active substance concentration may be approximately 5 to 80% by weight. Formulations in the form of dusts usually comprise 5 to 20% by weight of active substance, sprayable solutions approximately 2 to 20% by weight. In the case of granules, the active substance content depends partly on whether the active compound is in liquid or solid form and on which granulation auxiliaries, fillers and the like are being used.

Besides, the abovementioned active substance formulations comprise, if appropriate, the tackifiers, wetters, dispersants, emulsifiers, penetrants, solvents, fillers or carriers which are conventional in each case.

For use, the concentrates, which are present in commercially available form, are, if desired, diluted in the customary manner, for example in the case of wettable powders, emulsifiable concentrates, dispersions and in some cases also microgranules, using water. Preparations in the form of dusts and granules and sprayable solutions are usually not diluted any further with other inert substances prior to use.

The application rate required varies with the external conditions such as, inter alia, temperature and humidity. It may vary within wide limits, for example between 0.0005 and 10.0 kg/ha or more of active substance, but it is preferably between 0.001 and 5 kg/ha of active compound.

The active substances according to the invention, in their commercially available formulations and in the use forms prepared from these formulations, may be present in mixtures with other active substances such as insecticides, attractants, sterilants, acaricides, nematicides, fungicides, growth regulatory substances or herbicides.

The pesticides include, for example, phosphoric esters, carbamates, carboxylic esters, formamidines, tin compounds and materials produced by microorganisms.

Preferred components in mixtures are:

1. from the group of the phosphorus compounds acephate, azamethiphos, azinphos-ethyl, azinphos-methyl, bromophos, bromophos-ethyl, cadusafos (F-67825), chlorethoxyphos, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, dimethoate, disulfoton, EPN, ethion, ethoprophos, etrimfos, famphur, fenamiphos, fenitriothion, fensulfothion, fenthion, flupyrazofos, fonofos, formothion, fosthiazate, heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosphocarb (BAS-301), phosmet, phosphamidon, phoxim, pirimiphos, pirimiphos-ethyl, pirimiphos-methyl, profenofos, propaphos, proetamphos, prothiofos, pyraclofos, pyridapenthion, quinalphos, sulprofos, temephos, terbufos, tebupirimfos, tetrachlorvinphos, thiometon, triazophos, trichlorophon, vamidothion;

2. from the group of the carbamates alanycarb (OK-135), aldicarb, 2-sec-butylphenyl methylcarbamate (BPMC), carbaryl, carbofuran, carbosulfan, cloethocarb, benfuracarb, ethiofencarb, furathiocarb, HCN-801, isoprocarb, methomyl, 5-methyl-m-cumenylbutyryl(methyl)carbamate, oxamyl, pirimicarb, propoxur, thiodicarb, thiofanox, 1-methylthio(ethylideneamino)-N-methyl-N-(morpholinothio) carbamate (UC 51717), triazamate;

3. from the group of the carboxylic esters acrinathrin, allethrin, alphametrin, 5-benzyl-3-furylmethyl (E)-(1R)-cis-2,2-dimethyl-3-(2-oxothiolan-3-ylidenemethyl)cyclopropanecarboxylate, beta-cyfluthrin, alpha-cypermethrin, beta-cypermethrin, bioallethrin, bioallethrin ((S)-cyclopentylisomer), bioresmethrin, bifenthrin, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyfluthrin, cyhalothrin, cythithrin, cypermethrin, cyphenothrin, deltamethrin, empenthrin, esfenvalerate, fenfluthrin, fenpropathrin, fenvalerate, flubrocythrinate, flucythrinate, flumethrin, fluvalinate (D isomer), imiprothrin (S-41311), lambda-cyhalothrin, permethrin, phenothrin ((R) isomer), prallethrin, pyrethrins (natural products), resmethrin, tefluthrin, tetramethrin, theta-cypermethrin, tralomethrin, transfluthrin, zeta-cypermethrin (F-56701);

4. from the group of the amidines amitraz, chlordimeform;

5. from the group of the tin compounds cyhexatin, fenbutatin oxide;

6. others abamectin, ABG-9008, acequinocyl, azadirachtin, acetamiprid, *Anagrapha falcitera*, AKD-1022, AKD-3059, AKD-3088, AL-9811, ANS-118, azadirachtin, *Bacillus thuringiensis, Beauveria bassianea*, bensultap, bifenazate (D-2341), binapacryl, BJL-932, bromopropylate, BAJ-2740 (spirodiclofen), BTG-504, BTG-505, buprofezin, camphechlor, cartap, chlorobenzilate, chlorfenapyr, chlorfluazuron, 2-(4-chlorophenyl)-4,5-diphenylthiophene (UBI-T 930), chlorfentezine, chloproxyfen, clothianidin, chromafenozide (ANS-118), A-184699, clothianidine, 2-naphthylmethyl cyclopropanecarboxylate (Ro12-0470), cyromazin, CM-002X, DBI-3204, diacloden (thiamethoxam), diafenthiuron, DBI-3204, ethyl 2-chloro-N-(3,5-dichloro-4-(1,1,2,3,3,3-hexafluoro-1-propyloxy)phenyl) carbamoyl)-2-carboximidate, DDT, dicofol, diflubenzuron, N-(2,3-dihydro-3-methyl-1,3-thiazol-2-ylidene)-2,4-xylidine, dihydroxymethyldihydroxypyrrolidine, dinobuton, dinocap, diofenolan, DPX-062, emamectin benzoate (MK-244), endosulfan, ethiprole (sulfethiprole), ethofenprox, etoxazole (YI-5301), fenazaquin, fenoxycarb, fipronil, fluazuron, flumite (flufenzine, SZI-121), 2-fluoro-5-(4-(4-ethoxyphenyl)-4-methyl-1-pentyl)diphenylether (MTI 800), granulosis and nuclear polyhedrosis viruses, fenpyroximate, fenthiocarb, fluacrypyrim, flufenzine, flubenzimine, flubrocythrinate, flucycloxuron, flufenoxuron, flufenprox (ICI-A5683), flufenzine, fluproxyfen, FMC-F6028, gamma-HCH, halfenozide (RH-0345), halofenprox (MTI-732), hexaflumuron (DE_473), hexythiazox, HOI-9004, hydramethyinon (AC 217300), lufenuron, L-14165, imidacloprid, indokacarb (DPX-MP062), kanemite (AKD-2023), M-020, MTI-446, ivermectin, M-020, IKA-2000, IKI-220 (flonicamid), MKI-245, methoxyfenozide (Intrepid, RH-2485), milbemectin, NC-196, neemgard, nitenpyram (TI-304), 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), novaluron, NC-196, NNI-0001, nidintefuran, propargite, pyriproxyfen (S-71639), pirydaryl, protrifenbute, pyriproxyfen, NC-196, NC-1111, NNI-9768, novaluron (MCW-275), OK-9701, OK-9601, OK-9602, OK-9802, propargite, pymethrozine, pyridaben, pyrimidifen (SU-8801), R-195, RH-0345, RH-2485, RYI-210, S-1283, S-1833, SB7242, SI-8601, silafluofen, silomadine (CG-177), spinosad, spirodiclofen, SU-9118, tebufenozide, tebufenpyrad (MK-239), teflubenzuron, tetradifon, tetrasul, thiacloprid, thiocyclam, thiamethoxam, T1435, tolfenpyrad (OMI-88), triazamate (RH-7988), triflumuron, triethoxyspinosyn A, verbutin, vertalec (Mykotal), YI-5301 and Yi-6101.

The abovementioned components for combinations are known active substances, many of which are described in Ch.R Worthing, S. B. Walker, The Pesticide Manual, 12th Edition, British Crop Protection Council, Farnham 2000.

Fungicides which may be mentioned (as being suitable for combinations with the compounds of the formulae (I) and/or (II) according to the invention are, for example, the following products:

aldimorph, andoprim, anilazine, BAS 480F, BAS 450F, benalaxyl, benodanil, benomyl, binapacryl, bitertanol, bromuconazole, buthiobate, captafol, captan, carbendazim, carboxin, CGA 173506, cyprofuram, dichlofluanid, dichlomezin, diclobutrazole, diethofencarb, difenconazole (CGA 169374), difluconazole, dimethirimol, dimethomorph, diniconazole, dinocap, dithianon, dodemorph, dodine, edifenfos, ethirimol, etridiazot, fenarimol, fenfuram, fenpiclonil, fenpropidin, fenpropimorph, fentin acetate, fentin hydroxide, ferimzone (TF164), fluazinam, fluobenzimine, fluquinconazole, fluorimide, flusilazole, flutolanil, fluthafol, folpet, fosetyl aluminum, fuberidazole, fulsulfamide (MT-F 651), furalaxyl, furconazole, furmecyclox, guazatine, hexaconazole, ICI A5504, imazalil, imibenconazole, iprobenfos, iprodione, isoprothiolane, KNF 317, copper compounds, such as Cu oxychloride, oxine-Cu, Cu oxide, mancozeb, maneb, mepanipyrim (KIF 3535), metconazole, mepronil, metalaxyl, methasulfocarb, methfuro xam, MON 24000, myclobutanil, nabam, nitrothalido-propyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyroquilon, rabenzazole, RH7592, sulfur, tebuconazole, TF 167, thiabendazole, thicyofen, thiofanate-methyl, thiram, tolclofos-methyl, tolylfluanid, triadimefon, triadimenol, tricyclazole, tridemorph, triflumizol, triforine, validamycin, vinchiozolin, XRD 563, zineb, sodium dodecylsulfonate, sodium dodecylsulfate, sodium C13/C15-alcohol ether sulfonate, sodium cetostearyl phosphate ester, dioctyl sodium sulfosuccinate, sodium isopropylnaphthalenesulfonate, sodium methylenebisnaphthalenesulfonate, cetyltrimethlammonium chloride, salts of long-chain primary, secondary or tertiary amines, alkylpropyleneamine, laurylpyrimidinium bromide, ethoxylated quaternized fatty amines, alkyldimethylbenzylammonium chloride and 1-hydroxyethyl-2-alkylimidazoline.

The active substance content of the use forms prepared from the commercially available formulations may range from 0.00000001 up to 95% by weight of active substance, preferably between 0.00001 and 1% by weight.

Application is effected in a customary manner adapted to suit the use forms.

Therefore in further aspects of the invention there are provided the use of the compounds of the formula (I) or salts thereof and/or compounds of the formula (II) or salts thereof for controlling animal pests; and a method for controlling animal pests, comprises the step of directly or indirectly applying to the pest a compound of the formula (I) or (II) or a salt thereof.

The active substances according to the invention are also suitable for controlling endoparasites and ectoparasites in the human and veterinary medicine sector and/or in the field of animal keeping. The active substances according to the invention are applied here in a known manner, such as by oral administration in the form of, for example, tablets, capsules, drinks or granules, by dermal application in the form of, for example, dipping, spraying, pouring on and spotting on, and dusting, and by parenteral administration in the form of, for example, an injection.

Accordingly, the compounds of the formulae (I) and (II) according to the invention can also be employed particularly advantageously for the treatment of warm-blooded species, especially in livestock keeping (for example cattle, sheep, pigs and poultry such as chickens, geese and the like). In a preferred embodiment of the invention, the compounds, if appropriate in suitable formulations, are administered orally to the animals, if appropriate together with the drinking water or feed. Since excretion in the feces is efficient, the development of insects in the animals' feces can be prevented very easily in this manner. The dosages and formulations which are suitable in each case depend, in particular, on the species and the developmental stage of the productive livestock and also on the risk of infestation and can be determined readily and established by customary methods. For example, the compounds can be employed in cattle at dosages of 0.01 to 1 mg/kg of bodyweight.

In addition to the abovementioned application methods, the active compounds of the formulae (I) and (II) according to the invention have excellent systemic action. Accordingly, the active compounds can also be introduced into the plants via parts of the plant, both below ground and above ground (for example root, stolons, stem, trunk, leaf), if the active compounds are applied, in liquid or solid form, onto the plant and/or in the direct vicinity of the plant (for example granules in soil application, application in flooded rice paddies, trunk injection in the case of trees, stem bandages in the case of perennial plants).

Furthermore, the active compounds according to the invention, optionally in coformulation with fungicides, are particularly useful for the treatment of vegetative and generative plant propagation material, such as, for example, of seeds, for example of cereals, vegetables, cotton, rice, sugar beet and other crops and ornamental plants, of bulbs, seedlings and tubers of other crops and ornamental plants which are propagated vegetatively. The treatment can be carried out before sowing or before planting (for example by special seed coating techniques, by dressing in liquid or solid form or as a seed box treatment), during sowing or planting or after sowing or planting by special application techniques (for example furrow treatment). The amount of active compound used can vary within a relatively large range, depending on the application. In general, the application rates are between 1 g and 10 kg of active compound per hectare of soil surface. The treatment methods for plant propagation material and the plant propagation material treated in this manner are also provided by the invention.

The compounds of the formulae (I) and (II) can also be employed for controlling animal pests in crops of known genetically engineered plants or genetically engineered plants yet to be developed. As a rule, the transgenic plants are distinguished by especially advantageous properties, for example by resistances to particular crop protection agents, resistances to plant diseases or pathogens of plant diseases, such as particular insects or microorganisms such as fungi, bacteria or viruses. Other particular properties concern, for example, the harvested material with regard to quantity, quality, storage properties, composition and specific constituents. Thus, transgenic plants are known where the starch content is increased, or the starch quality is altered, or where the harvested material has a different fatty acid composition.

The use in economically important transgenic crops of useful plants and ornamentals is preferred, for example of cereals such as wheat, barley, rye, oats, millet, rice, cassava and maize or else crops of sugar beet, cotton, soya, oilseed rape, potatoes, tomatoes, peas and other types of vegetables.

When used in transgenic crops, in particular those which have resistances to insects, effects are frequently observed, in addition to the effects against harmful organisms to be observed in other crops, which are specific for application in the transgenic crop in question, for example an altered or specifically widened spectrum of pests which can be controlled, or altered application rates which may be employed for application.

The invention therefore also relates to the use of compounds of the formulae (I) and (II) for controlling harmful organisms, in particular animal pests, in transgenic crop plants.

In addition to their lethal effect on pests, the compounds of the formulae (I) and (II) also have a pronounced repellant effect.

A repellant for the purpose of the compound is a substance or substance mixture which has a warding-off or fending-off effect on other life organisms, in particular harmful pests and nuisance pests. The term also encompasses effects such as the antifeeding effect, where the intake of feed is disturbed or prevented (antifeedant effect), suppression of oviposition, or an effect on the development of the population.

The invention therefore also provides the use of compounds of the formulae (I) and (II) for achieving the abovementioned effects, in particular in the case of the pests stated in the biological examples.

The invention also provides a method for fending off, or warding off, harmful organisms, where one or more compounds of the formulae (I) and (II) are applied to the site from which the harmful organisms are to be fended off or warded off.

In the case of a plant, application may mean, for example, a treatment of the plant, but also of the seed.

As regards the effect on populations, it is interesting to note that effects can also be observed in succession during the development of a population, where summation may take place. In such a case, the individual effect itself may only have an efficacy of markedly less than 100% but in total an efficacy of 100% is still achieved in the end.

Moreover, the compounds of the formulae (I) and (II) are distinguished by the fact that the composition is usually applied earlier than in the case of a direct control, if the abovementioned effects are to be exploited. The effect frequently lasts over a long period, so that a duration of action of over 2 months is achieved.

The effects are observed in insects, arachnids and the other abovementioned pests.

The use of the compounds according to the invention embraces, in addition to direct application onto the pests, any other application in which compounds of the formulae (I) and (II) act on the pests. Such indirect applications can, for example, be the use of compounds which, for example in the soil, the plant or the pest, decompose into compounds of the formulae (I) and (II) and/or are degraded into compounds of the formulae (I) and (II).

The content of the German Patent Application 101 468 73.3, whose priority the present application claims, and the appended abstract is incorporated herein by reference.

The examples below serve to illustrate the invention.

I. CHEMICAL EXAMPLES

EXAMPLE A

Preparation of N-cyclohexylthio-(4-trifluoromethyl)nicotinamide

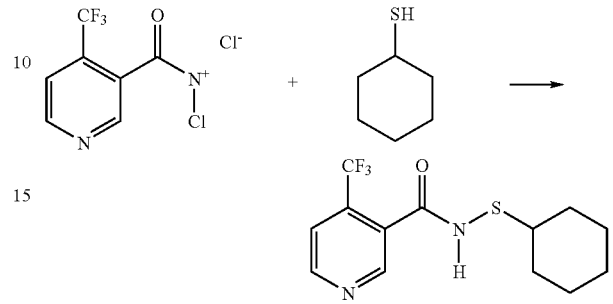

Cyclohexylmercaptan (1 g 0.009 mol) and triethylamine (1.2 ml=0.009 mol) were initially charged in 20 ml of acetonitrile, and the supernatant solution of N-chloro-4-trifluoromethylnicotinamide hydrochloride (2.24 g=0.009 mol) in triethylamine (1.2 ml=0.009 mol) in 10 ml of acetonitrile was added dropwise. The mixture was stirred at room temperature for three hours. For work-up, the acetonitrile was distilled off, the residue was triturated with acetone and the precipitate was filtered off with suction. The precipitate was washed with acetone and the organic phases were then combined, the solvent was removed and the oil that remained was purified by silica gel chromatography using ethyl acetate. This gave 1.64 g (63%) of N-cyclohexylthio-(4-trifluoromethyl)nicotinamide as a clear oil.

EXAMPLE B

Preparation of N-(2-butylthio)-(4-trifluoromethyl)nicotinamide

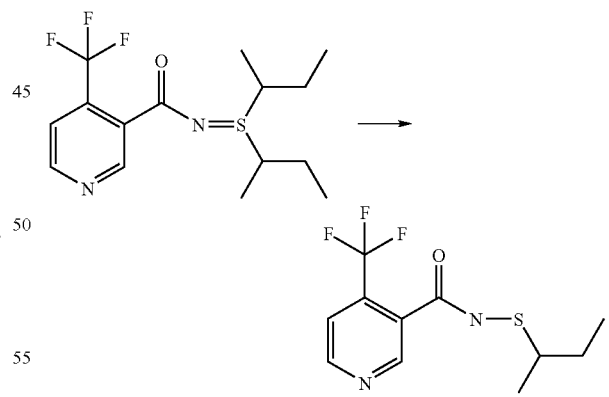

S,S-2-N-(4-trifluoromethyl)nicotinoylsulfimide (0.5 g=0.0015 mol) was heated at 100° C. for 5 hours. The reaction mixture was taken up in ethyl acetate and filtered through a pad of silica gel. The solvent was removed under reduced pressure, which gave 0.26 g (62.5%) of N-(2-butylthio)-(4-trifluoromethyl)nicotinamide as a colorless oil (NMR (DMSO): 9.75, s, 1H; 8.95, d, 6 Hz, 1H; 8.84, s, 1H; 7.86, d, 6 Hz, 1H; 3.00, m, 1H; 1.60, m, 1H; 1.44, m, 1H; 1.20, d, 7 Hz, 3H; 0.96, t, 7 Hz, 1 H).

EXAMPLE C

Preparation of N-(isopropyl)-(4-trifluoromethyl)nicotinamide and compound (X)

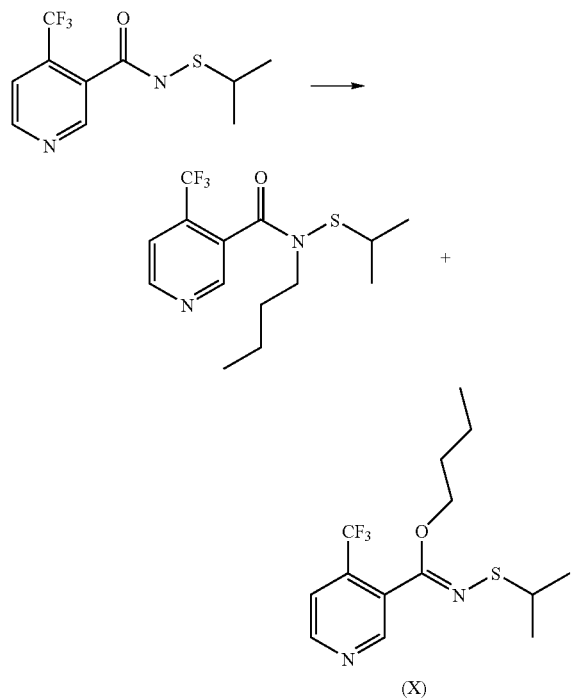

3.95 g (0.015 mol) of triphenylphosphine were dissolved in 100 ml of THF. Below 5° C., 2.35 ml (0.015 mol) of diethyl azodicarboxylate were added dropwise and the solution was then stirred at room temperature for 20 minutes. 1.35 ml of 1-butanol were then added dropwise, and the mixture was stirred at room temperature. After 5 minutes, a solution of 2.65 g of N-isopropylthio-(4-trifluoromethyl)nicotinamide in 25 ml of THF was added, and the mixture was stirred at room temperature for 20 hours. The substance mixture was then concentrated and purified on a column using n-heptane: ethyl acetate 1:1. 0.17 g (5%) of N-butyl-N-isopropylthio-(4-trifluoromethyl)nicotinamide and 1.2 g (37%) of compound (X) were isolated as oils.

EXAMPLE D

Preparation of N-benzylthio-N-cyclohexyl-(4-trifluoromethyl)nicotinamide

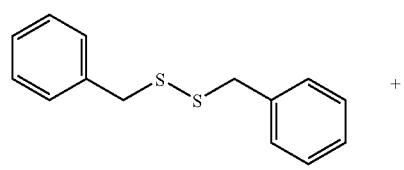

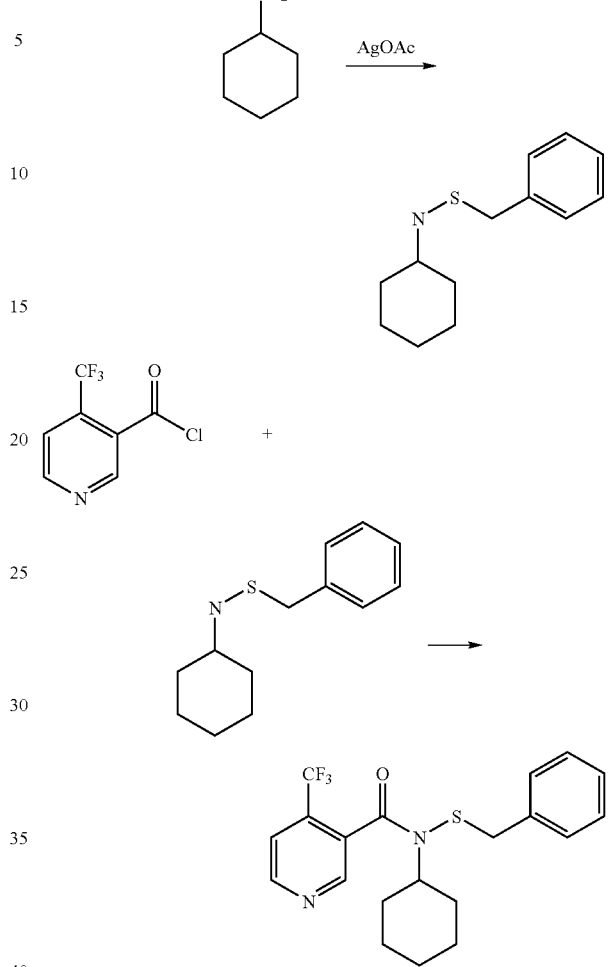

0.81 g (0.0033 mol) of dibenzyl disulfide and 1.1 g (0.0066 mol) of silver acetate were initially charged in 40 ml of ethyl acetate, the mixture was cooled to 0–5° C. and 1.9 ml (0.016 mol) of cyclohexylamine were then added dropwise. The reaction was slightly exothermic. The ice-bath was removed and the flask was wrapped in aluminum foil and stirred at room temperature overnight. The mixture was then filtered, the solvent was removed and the reaction mixture was taken up in diethyl ether and water, and insoluble material was filtered off. The organic phase was washed with water and dried and the solvent was then removed. 0.15 g (18.5%) of the product N-(cyclohexyl)-N-(benzylthio)amine was isolated as a wax. 0.14 g (0.0006 mol) of N-cyclohexyl-N-(benzylthio)amine and 0.16 ml (0.0011 mol) of triethylamine were dissolved in 2.5 ml of THF, and 0.22 g (0.001 mol) of (4-trifluoromethyl)-nicotinoyl chloride was then added dropwise. The reaction mixture was stirred at room temperature for 4 hours. For work-up, ethyl acetate and water were added, the organic phase was concentrated and the residue was then chromatographed on silica gel using ethyl acetate:n-heptane 2:3. This gave 0.12 g (51%) of N-benzylthio-N-cyclohexyl-(4-trifluoromethyl)nicotinamide.

The compounds listed in the tables below are prepared in a similar manner.

TABLE 1

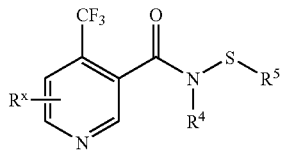

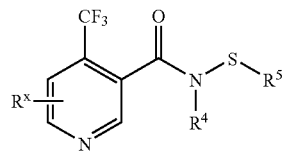

| Example No. | Rˣ | R⁴ | R⁵ | m.p. (° C.) |
|---|---|---|---|---|
| 1 | | H | cyclopentyl | Oil |
| 2 | | H | phenyl | Oil |
| 3 | | ethyl | phenyl | Oil |
| 4 | | 2-propyl | phenyl | Oil |
| 5 | | H | 4-methylphenyl | |
| 6 | | 2-propyl | 4-methylphenyl | Oil |
| 7 | | H | 2-bromophenyl | |
| 8 | | H | pentafluorophenyl | |
| 9 | | H | 2-chlorophenyl | |
| 10 | | H | 2,5-dichlorophenyl | |
| 11 | | H | 2,6-dichlorophenyl | |
| 12 | | ethyl | 2,6-dichlorophenyl | |
| 13 | | methyl | 2,6-dichlorophenyl | |
| 14 | | H | 2-methoxyphenyl | |
| 15 | | H | 2-isopropyphenyl | |
| 16 | | H | 2-methylphenyl | |
| 17 | | H | 3-chlorophenyl | |
| 18 | | H | 4-chlorophenyl | 120 |
| 19 | | H | 3,4-dichlorophenyl | |
| 20 | | H | 3-methoxyphenyl | |
| 21 | | H | 3-methylphenyl | |
| 22 | | H | 4-bromophenyl | |
| 23 | | H | 4-fluorophenyl | 106 |
| 24 | | H | 4-chlorophenyl | |
| 25 | | H | 4-acetamidophenyl | |
| 26 | | H | 4-methoxyphenyl | |
| 27 | | H | t-butyl | |
| 28 | | H | t-amyl | |
| 29 | | H | 2-propyl | 86 |
| 30 | | H | methyl | |
| 31 | | H | benzyl | |
| 32 | | H | 2-chloro-benzyl | |
| 33 | | H | 4-chloro-benzyl | |
| 34 | | H | 4-methoxy-benzyl | |
| 35 | | H | methyl-2-acetyl | |
| 36 | | H | ethyl-2-acetyl | |
| 37 | | H | 2-methyl-1-propyl | |
| 38 | | H | 2-methyl-1-butyl | Oil |
| 39 | | cyclohexyl | 2-methyl-1-butyl | |
| 40 | | H | 1-dodecyl | |
| 41 | | H | 1-nonyl | |
| 42 | | H | ethyl | |
| 43 | | H | 2-phenyl ethyl | |
| 44 | | H | allyl | Oil |
| 45 | | H | 3-methyl-1-butyl | Oil |
| 46 | | H | propyl | |
| 47 | | H | 1-butyl | |
| 48 | | H | 1-pentyl | Oil |
| 49 | | H | 1-hexyl | Oil |
| 50 | | H | 1-heptyl | Oil |
| 51 | | H | 1-octyl | |
| 52 | | H | 1-nonyl | |
| 53 | | H | 2-imidazoyl | |
| 54 | | H | 1-methyl-2-imidazoyl | |
| 55 | | H | 2-benzimidazoyl | |
| 56 | | H | 2-benzoxazoyl | |
| 57 | | H | 6-ethoxy-2-benzoxazoyl | |
| 58 | | H | 5-chloro-2-benzoxazoyl | |
| 59 | | H | 3,4,5,6-tetrahydropyrimidyl | |
| 60 | | H | 2-pyrimidyl | |
| 61 | | H | 4,6-dimethyl-2-pyrimidyl | |
| 62 | | H | 2-pyridyl | |
| 63 | | H | 4-pyridyl | |
| 64 | | H | 7-trifluoromethyl-4-quinolinyl | |
| 65 | | H | 2,6-dimethylphenyl | |
| 66 | | H | 2-ethyl-phenyl | |
| 67 | | H | 2-methyl-3-furyl | |
| 68 | | H | 4-phenyl-2-thiazoyl | |
| 69 | | H | 4-t-butyl-phenyl | |
| 70 | | H | N-(4-methyl-phenyl)acetamide | |
| 71 | | H | 4-aza-2-benzimidazoyl | |
| 72 | | H | 2(5-methyl-1,3,4 thiadiazoyl) | |
| 73 | | H | 2,4-dichlorobenzyl | |
| 74 | | H | 3,4-dichlorobenzyl | |
| 75 | | H | 4-methyl-benzyl | |
| 76 | | H | 3-fluoro-phenyl | |
| 77 | | H | 1,3,4-thiadiazoyl | |
| 78 | | H | 4-fluoro-benzyl | |
| 79 | | H | 3-(trifluoromethyl)phenyl | |
| 80 | | H | 2-fluorophenyl | |
| 81 | | H | 2,4-dichlorophenyl | |
| 82 | | H | 3,5-dichlorophenyl | |
| 83 | | H | 4-i-propylphenyl | |
| 84 | | H | 4-trifluoromethyl-benzyl | 119 |
| 85 | | H | 3-trifluoromethylbenzyl | Oil |
| 86 | | H | 2-pydidylmethyl | |
| 87 | | H | 4-trifluoromethoxybenzyl | |
| 88 | | H | 2-chloro-6-fluorobenzyl | |
| 89 | | H | 3-(4-chlorophenyl)-1,2,4 triazoyl | |
| 90 | | H | 3,4-dimethoxyphenyl | |
| 91 | | H | 3-butanoyl | |
| 92 | | H | 5-phenyl-1,3,4-oxadiazoyl | |
| 93 | | H | 2-thienylmethyl | Oil |
| 94 | | H | 4-trifluoro-methylpyri-2-yl | |
| 95 | | H | 3-chloro-5-trifluoromethyl-pydir2-yl | |
| 96 | | H | dimethylaminoethyl | |
| 97 | | H | 3-trifluoromethyl-pyrid-2-yl | |
| 98 | | H | cyclopropyl | Oil |
| 99 | | H | morpholin-4-ylmethyl | |
| 100 | | H | 4-pyrimidyl | |
| 101 | | H | 5-methyl-4H-1,2,4-triazoyl | |
| 102 | | H | cyclobutyl | |
| 103 | | 4-fluoro-phenyl | cyclobutyl | |
| 104 | | benzyl | cyclobutyl | |
| 105 | | methyl | cyclobutyl | |
| 106 | | ethyl | cyclobutyl | |
| 107 | | 2-propyl | cyclobutyl | |
| 108 | | cyclohexyl | cyclobutyl | |

TABLE 1-continued

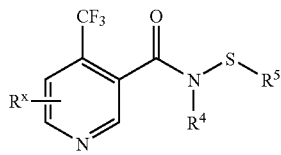

| Example No. | $R^x$ | $R^4$ | $R^5$ | m.p. (° C.) |
|---|---|---|---|---|
| 109 | | butyl | cyclobutyl | |
| 110 | 2,6-dichloro | H | 2-nitrophenyl | 240 |
| 111 | | H | hex-1-en-5-yl | |
| 112 | | H | 4-chloro-phenyl | |
| 113 | | H | 2,5-dimethylphenyl | |
| 114 | | H | 2-(methoxy-carbonyl)ethyl | |
| 115 | | H | 2-(trimethyl-silyl)ethyl | Oil |
| 116 | | H | 2-furylmethyl | Oil |

TABLE 2

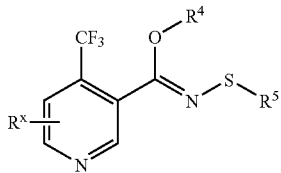

| Example No. | $R^x$ | $R^4$ | $R^5$ | m.p. (° C.) |
|---|---|---|---|---|
| 117 | | but-1-yl | isopropyl | |
| 118 | | prop-1-yl | isopropyl | |
| 119 | | 1-methylprop-1-yl | isopropyl | |
| 120 | | 2-vinyloxyeth-1-yl | isopropyl | |
| 121 | | pent-4-en-1-yl | isopropyl | |
| 122 | | 4-methyloxybut-1-yl | isopropyl | |
| 123 | | 4-methylthiobut-1-yl | isopropyl | |
| 124 | | 3-nitrobut-1-yl | isopropyl | |

B. FORMULATION EXAMPLES a) A dust is obtained by mixing 10 parts by weight of active substance and 90 parts by weight of talc as inert material and comminuting the mixture in a hammer mill.

b) A wettable powder which is readily dispersible in water is obtained by mixing 25 parts by weight of active substance, 65 parts by weight, of kaolin-containing quartz as inert material, 10 parts by weight of potassium lignosulfonate and 1 part by weight of sodium oleoylmethyltaurinate as wetter and dispersant and grinding the mixture in a pinned disk mill.

c) A dispersion concentrate which is readily dispersible in water is prepared by mixing 40 parts by weight of active substance with 7 parts by weight of a sulfosuccinic monoester, 2 parts by weight of a sodium lignosulfonate and 51 parts by weight of water and grinding the mixture in a ball mill to a fineness of below 5 microns.

d) An emulsifiable concentrate can be prepared from 15 parts by weight of active substance, 75 parts by weight of cyclohexane as solvent and 10 parts by weight of oxyethylated nonylphenol (10 EO) as emulsifier.

e) Granules can be prepared from 2 to 15 parts by weight of active substance and an inert granule carrier material such as attapulgite, pumice granules and/or quartz sand. It is expedient to use a suspension of the wettable powder of Example b) with a solids content of 30%, which is sprayed onto the surface of attapulgite granules, and these are dried and mixed intimately. The wettable powder amounts to approx. 5% by weight and the inert carrier material to approx. 95% by weight of the finished granules.

C. BIOLOGICAL EXAMPLES

In Examples 1 and 2 below, compounds are considered to be active when, at a concentration of 500 ppm (based on the content of active compound) or less, they have an effect on the harmful organisms of 50% or more.

EXAMPLE 1

Germinated field bean seeds (*Vicia faba*) with seed roots were transferred into brown glass bottles filled with tap water and then populated with about 100 black bean aphids (*Aphis fabae*). Plants and aphids were then dipped into an aqueous solution of the formulated preparation to be examined for 5 seconds. After they had drained, plants and animals were stored in a climatized chamber (16 hours of light/day, 25° C., 40–60% relative atmospheric humidity). After 3 and 6 days of storage, the mortality of the preparation on the aphids was determined. The compounds of the following examples were active: A, B, C, 1, 2, 3, 4, 6, 18, 23, 29, 38, 44, 45, 48, 49, 50, 84, 85, 98, 115, 116, 124.

EXAMPLE 2

Germinated field bean seeds (*Vicia faba*) with seed roots were transferred into brown glass bottles filled with tap water. Four milliliters of an aqueous solution of the formulated preparation to be examined were pipetted into the brown glass bottle. The field bean was then heavily populated with about 100 black bean aphids (*Aphis fabae*). Plants and aphids were then stored in a climatized chamber (16 hours of light/day, 25° C., 40–60% relative atmospheric humidity). After 3 and 6 days of storage, the root-systemic effect of the preparation as aphid mortality was determined. The compounds of the following examples were active: A, B, C, 1, 2, 3, 4, 6, 18, 23, 29, 38, 44, 45, 48, 49, 50, 84, 85, 98, 115, 116, 124.

What is claimed is:

1. A compound of the formula (I) or a salt thereof

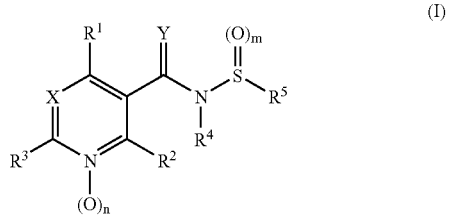

where the symbols and indices are as defined below:
X is =CH—;
Y is =O or =S;
n is 0 or 1;
m is 0;
$R^1$ is $(C_1-C_6)$-alkyl, $(C_1-C_6)$haloalkyl, —S(halogen)$_5$ or halogen, where one or two CH$_2$ groups may be replaced by —O— or —S— or —N($C_1-C_6$)-alkyl, with the proviso that heteroatoms may not be adjacent;

$R^2$, $R^3$ independently of one another are hydrogen, $(C_1-C_6)$-alkyl, $(C_1-C_6)$-haloalkyl or halogen, where one or two CH$_2$ groups maybe replaced by —O— or —S— or —N$(C_1-C_6)$-alkyl, with the proviso that heteroatoms may not be adjacent;

$R^4$ is hydrogen, $(C_1-C_{10})$-alkyl, $(C_3-C_{10})$-cycloalkyl, $(C_3-C_{10})$-alkenyl, $(C_3-C_{10})$-alkynyl, $(C_6-C_{14})$-aryl, $(C_3-C_{10})$-heterocyclyl or $(C_1-C_{10})$-alkanoyl, where the radicals mentioned may be unsubstituted or mono- or polysubstituted;

$R^5$ is hydrogen, $(C_1-C_{10})$-alkyl, $(C_3-C_{10})$-alkenyl-, $(C_3-C_{10})$-alkynyl, $(C_3-C_8)$-cycloalkyl, $(C_4-C_8)$-cycloalkenyl, $(C_8-C_{10})$-cycloalkynyl, aryl or heterocyclyl, where the radicals mentioned may be unsubstituted or mono- or polysubstituted.

2. A compound of the formula (II) or a salt thereof

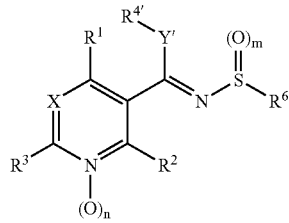

(II)

where the symbols and indices are as defined below:
X is =CH—
Y' is —O— or —S—;
n is 0 or 1;
m is 0;
$R^1$ is $(C_1-C_6)$-alkyl-, $(C_1-C_6)$-haloalkyl, —S(halogen)$_5$ or halogen, where one or two CH$_2$ groups may be replaced by —O— or —S— or —N$(C_1-C_6)$-alkyl, with the proviso that heteroatoms may not be adjacent;

$R^2$, $R^3$ independently of one another are hydrogen, $(C_1-C_6)$-alkyl, $(C_1-C_6)$-haloalkyl or halogen, where one or two CH$_2$ groups may be replaced by —O— or —S— or —N$(C_1-C_6)$-alkyl, with the proviso that heteroatoms may not be adjacent;

$R^{4'}$ is hydrogen, $(C_1-C_{10})$-alkyl, $(C_3-C_{10})$-cycloalkyl, $(C_3-C_{10})$-alkenyl, $(C_3-C_{10})$-alkynyl, $(C_6-C_{14})$-aryl or $(C_3-C_{10})$-heterocyclyl, where the radicals mentioned may be unsubstituted or mono- or polysubstituted; and $R^6$ is hydrogen, $(C_1-C_{10})$-alkyl, $(C_3-C_{10})$-alkenyl, $(C_3-C_{10})$-alkynyl, $(C_3-C_8)$-cycloalkyl, $(C_4-C_8)$-cycloalkenyl, $(C_8-C_{10})$-cycloalkynyl, aryl or heterocyclyl, where the radicals mentioned may be unsubstituted or mono- or polysubstituted.

3. A compound of the formula (I) or a salt thereof as claimed in claim 1 where $R^1$ is SF$_5$, CHF$_2$, CF$_2$Cl or CF$_3$.

4. A compound of the formula (I) or a salt thereof

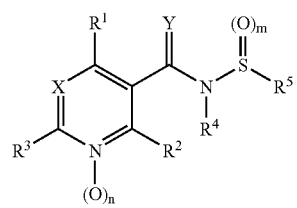

(I)

where X is =CH—, Y is =O, m and n are 0, $R^1$ is CF$_3$, $R^2$, $R^3$ and $R^4$ are hydrogen and $R^5$ is $(C_1-C_{10})$-alkyl, $(C_2-C_{10})$-alkenyl, $(C_2-C_{10})$-alkynyl, $(C_3-C_8)$-cycloalkyl, $(C_4-C_8)$-cycloalkenyl, $(C_8-C_{10})$-cycloalkynyl, aryl or heterocyclyl, where the radicals mentioned may be unsubstituted or mono- or polysubstituted.

5. A compound of the formula (I) or a salt thereof as claimed in claim 1 where $R^5$ is a radical of the formula IIa

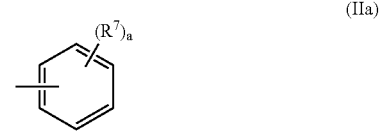

(IIa)

where the symbols and indices are as defined below:
a is 0, 1, 2, 3 or 4;
$R^7$ are identical or different $R^8$, or two radicals $R^7$ together with the atoms to which they are attached form a three- to eight-membered saturated or unsaturated ring system which is unsubstituted or substituted by one or more radicals $R^8$ and which may also contain further heteroatoms, selected from the group consisting of O, N, S, SO and SO$_2$;

$R^8$ are identical or different $R^9$, $R^{10}$, —C(W)R$^9$, —C(=NOR$^9$)R$^9$, —C(=NNR$^9_2$)R$^9$, —C(=W)OR$^9$, —C(=W)NR$^9_2$, —OC(=W)R$^9$, —OC(=W)OR$^9$, —NR$^9$C(=W)R$^9$, —N[C(=W)R$^9$]$_2$, —NR$^9$C(=W) OR$^9$, —C(=W)NR$^9$—NR$^9_2$, —C(=W)NR$^9$—NR$^9$[C (=W)R$^9$], —NR$^9$—C(=W)NR$^9_2$, —NR$^9$—NR$^9$C (=W)R$^9$, —NR$^9$—N[C(=W)R$^9$]$_2$, —N[(C=W) R$^9$]—NR$^9_2$, —NR$^9$—N[(C=W)WR$^9$], —NR$^9$ [(C=W)NR$^9_2$], —NR$^9$(C=NR$^9$)R$^9$, —NR$^9$(C=NR$^9$) NR$^9_2$, —O—NR$^9_2$, —O—NR$^9$(C=W)R$^9$, —SO$_2$NR$^9_2$, —NR$^9$SO$_2$R$^9$, —SO$_2$OR$^9$, —OSO$_2$R$^9$, —OR$^9$, —NR$^9_2$, —SR$^9$, —SiR$^9_3$, —PR$^9_2$, —P(=W) R$^9_2$, —SOR$^9$, —SO$_2$R$^9$, —PW$_2$R$^9_2$, —PW$_3$R$^9_2$ or two radicals $R^8$ together are (=W), (=N—R$^9$), (=CR$^9_2$), (=CHR$^9$) or (=CH$_2$);

W is =O or =S;

$R^9$ are identical or different $(C_1-C_6)$-alkyl, $(C_2-C_6)$-alkenyl, $(C_2-C_6)$-alkynyl, $(C_3-C_8)$-cycloalkyl, $(C_4-C_8)$-cycloalkenyl, $(C_3-C_8)$-cycloalkyl-$(C_1-C_4)$-alkyl, $(C_4-C_8)$-cycloalkenyl-$(C_1-C_4)$-alkyl, $(C_3-C_8)$-cycloalkyl-$(C_2-C_4)$-alkenyl, $(C_4-C_8)$-cycloalkenyl-$(C_2-C_4)$-alkenyl, $(C_1-C_8)$-alkyl-$(C_3-C_8)$-cycloalkyl, $(C_2-C_6)$-alkenyl-$(C_3-C_8)$-cycloalkyl, $(C_2-C_6)$-alkynyl-$(C_3-C_8)$-cycloalkyl, $(C_1-C_6)$-alkyl-$(C_4-C_8)$-cycloalkenyl, $(C_2-C_6)$alkenyl-$(C_4-C_8)$-cycloalkenyl, aryl, heterocyclyl; where the radicals mentioned are unsubstituted or substituted by one or more radicals $R^{10}$ and two radicals $R^9$ together may form a ring system;

$R^{10}$ are identical or different halogen, cyano, nitro, hydroxyl, thio, amino, formyl, $(C_1-C_6)$-alkanoyl, $(C_1-C_6)$-alkoxy, $(C_3-C_6)$-alkenyloxy, $(C_3-C_6)$-alkynyloxy, $(C_1-C_6)$-haloalkyloxy, $(C_3-C_6)$-haloalkenyloxy, $(C_3-C_6)$-haloalkynyloxy, $(C_3-C_8)$-cycloalkoxy, $(C_4-C_8)$-cycloalkenyloxy, $(C_3-C_8)$-halocycloalkoxy, $(C_4-C_8)$-halocycloalkenyloxy, $(C_3-C_8)$-cycloalkyl-$(C_1-C_4)$-alkoxy, $(C_4-C_8)$-cycloalkenyl-$(C_1-C_4)$-alkoxy, $(C_3-C_8)$-cycloalkyl-$(C_2-C_4)$-alkenyloxy, $(C_4-C_8)$-cycloalkenyl-$(C_1-C_4)$-alkenyloxy, $(C_1-C_6)$-alkyl-$(C_3-C_8)$-cycloalkoxy, $(C_2-C_6)$-alkenyl-$(C_3-C_8)$-cycloalkoxy, $(C_2-C_6)$-alkynyl-$(C_3-C_8)$-cycloalkoxy, $(C_1-C_6)$-alkyl-$(C_4-C_8)$-cycloalkenyloxy, $(C_2-C_6)$-alkenyl-($C_4$–$C_8$)-cycloalkenyloxy, ($C_1$–$C_4$)-alkoxy-($C_1$–$C_6$)-alkoxy, ($C_1$–$C_4$)-alkoxy-($C_3$–$C_6$)-alkenyloxy, carbamoyl, ($C_1$–$C_6$)-mono- or -dialkylcarbamoyl, ($C_1$–$C_6$)-mono- or -dihaloalkylcarbamoyl, ($C_3$–$C_8$)-mono- or -dicycloalkylcarbamoyl, ($C_1$–$C_6$)-alkoxycarbonyl, ($C_3$–$C_8$)-cycloalkoxycarbonyl, ($C_1$–$C_6$)-alkanoyloxy, ($C_3$–$C_8$)-cycloalkanoyloxy, ($C_1$–$C_6$)-haloalkoxycarbonyl, ($C_1$–$C_6$)-haloalkanoyloxy, ($C_1$–$C_6$)-alkanoylamino, ($C_1$–$C_6$)-haloalkanoylamino, ($C_2$–$C_8$)-alkenoylamino, ($C_3$–$C_8$)-cycloalkanoylamino, ($C_3$–$C_8$)-cycloalkyl-($C_1$–$C_4$)-alkanoylamino, ($C_1$–$C_6$)-alkylthio, ($C_3$–$C_6$)alkenylthio, ($C_3$–$C_6$)-alkynylthio, ($C_1$–$C_6$)-haloalkylthio, ($C_3$–$C_6$)-haloalkenylthio, ($C_3$–$C_6$)-haloalkynylthio, ($C_3$–$C_8$)-cycloalkylthio, ($C_4$–$C_8$)-cycloalkenylthio, ($C_3$–$C_8$)-halocycloalkylthio, ($C_4$–$C_8$)-halocycloalkenylthio, ($C_3$–$C_8$)-cycloalkyl-($C_1$–$C_4$)-alkylthio, ($C_4$–$C_8$)-cycloalkenyl-($C_1$–$C_4$)-alkylthio, ($C_3$–$C_8$)-cycloalkyl-($C_3$–$C_4$)-alkenylthio, ($C_4$–$C_8$)-cycloalkenyl-($C_3$–$C_4$)-alkenylthio, ($C_1$–$C_6$)-alkyl-($C_3$–$C_8$)-cycloalkylthio, ($C_2$–$C_6$)-alkenyl-($C_3$–$C_8$)-cycloalkylthio, ($C_2$–$C_6$)-alkynyl-($C_3$–$C_8$)-cycloalkylthio, ($C_1$–$C_6$)-alkyl-($C_4$–$C_8$)-cycloalkenylthio, ($C_2$–$C_6$)-alkenyl-($C_4$–$C_8$)-cycloalkenylthio, ($C_1$–$C_6$)-alkylsulfinyl, ($C_3$–$C_6$)-alkenylsulfinyl, ($C_3$–$C_6$)-alkynylsulfinyl, ($C_1$–$C_6$)-haloalkylsulfinyl, ($C_3$–$C_6$)-haloalkenylsulfinyl, ($C_3$–$C_6$)-haloalkynylsulfinyl, ($C_3$–$C_8$)-cycloalkylsulfinyl, ($C_4$–$C_8$)-cycloalkenylsulfinyl, ($C_3$–$C_8$)-halocycloalkylsulfinyl, ($C_4$–$C_8$)-halocycloalkenylsulfinyl, ($C_3$–$C_8$)-cycloalkyl-($C_1$–$C_4$)-alkylsulfinyl, ($C_4$–$C_8$)-cycloalkenyl-($C_1$–$C_4$)-alkylsulfinyl, ($C_3$–$C_8$)-cycloalkyl-($C_3$–$C_4$)-alkenylsulfinyl, ($C_4$–$C_8$)-cycloalkenyl-($C_3$–$C_4$)-alkenylsulfinyl, ($C_1$–$C_6$)-alkyl-($C_3$–$C_8$)-cycloalkylsulfinyl, ($C_2$–$C_6$)-alkenyl-($C_3$–$C_8$)-cycloalkylsulfinyl, ($C_2$–$C_6$)-alkynyl-($C_3$–$C_8$)-cycloalkylsulfinyl, ($C_1$–$C_6$)-alkyl-($C_4$–$C_8$)-cycloalkenylsulfinyl, ($C_2$–$C_6$)-alkenyl-($C_4$–$C_8$)-cycloalkenylsulfinyl, ($C_1$–$C_6$)-alkylsulfonyl, ($C_3$–$C_6$)-alkenylsulfonyl, ($C_3$–$C_6$)-alkynylsulfonyl, ($C_1$–$C_6$)-haloalkylsulfonyl, ($C_3$–$C_6$)-haloalkenylsulfonyl, ($C_3$–$C_6$)-haloalkynylsulfonyl, ($C_3$–$C_8$)-cycloalkylsulfonyl, ($C_4$–$C_8$)-cycloalkenylsulfonyl, ($C_3$–$C_8$)-halocycloalkylsulfonyl, ($C_4$–$C_8$)-halocycloalkenylsulfonyl, ($C_3$–$C_8$)-cycloalkyl-($C_1$–$C_4$)-alkylsulfonyl, ($C_4$–$C_8$)-cycloalkenyl-($C_1$–$C_4$)-alkylsulfonyl, ($C_3$–$C_8$)-cycloalkyl-($C_3$–$C_4$)-alkenylsulfonyl, ($C_4$–$C_8$)-cycloalkenyl-($C_3$–$C_4$)-alkenylsulfonyl, ($C_1$–$C_6$)alkyl-($C_3$–$C_8$)-cycloalkylsulfonyl, ($C_2$–$C_6$)-alkenyl-($C_3$–$C_8$)-cycloalkylsulfonyl, ($C_2$–$C_6$)-alkynyl-($C_3$–$C_8$)-cycloalkylsulfonyl, ($C_1$–$C_6$)-alkyl-($C_4$–$C_8$)-cycloalkenylsulfonyl, ($C_2$–$C_6$)alkenyl-($C_4$–$C_8$)-cycloalkenylsulfonyl, ($C_1$–$C_6$)-dialkylamino, ($C_1$–$C_6$)-alkylamino, ($C_3$–$C_6$)-alkenylamino, ($C_3$–$C_6$)-alkynylamino, ($C_1$–$C_6$)-haloalkylamino, ($C_3$–$C_6$)-haloalkenylamino, ($C_3$–$C_6$)-haloalkynylamino, ($C_3$–$C_8$)-cycloalkylamino, ($C_4$–$C_8$)-cycloalkenylamino, ($C_3$–$C_8$)-halocycloalkamino, ($C_4$–$C_8$)-halocycloalkenylamino, ($C_3$–$C_8$)-cycloalkyl-($C_1$–$C_4$)-alkylamino, ($C_4$–$C_8$)-cycloalkenyl-($C_1$–$C_4$)-alkylamino, ($C_3$–$C_8$)cycloalkyl-($C_3$–$C_4$)-alkenylamino, ($C_4$–$C_8$)-cycloalkenyl-($C_3$–$C_4$)-alkenylamino, ($C_1$–$C_6$)-alkyl-($C_3$–$C_8$)-cycloalkylamino, ($C_2$–$C_6$)-alkenyl-($C_3$–$C_8$)-cycloalkylamino, ($C_2$–$C_6$)-alkynyl-($C_3$–$C_8$)-cycloalkylamino, ($C_1$–$C_6$)-alkyl-($C_4$–$C_8$)-cycloalkenylamino, ($C_2$–$C_6$)-alkenyl-($C_4$–$C_8$)-cycloalkenylamino, ($C_1$–$C_6$)-trialkylsilyl, aryl, aryloxy, arylthio, arylsulfinyl, arylsulfonyl, arylamino, aryl-($C_1$–$C_4$)-alkoxy, aryl-($C_3$–$C_4$)-alkenyloxy, aryl-($C_1$–$C_4$)-alkylthio, aryl-($C_1$–$C_4$)-alkylsulfinyl, aryl-($C_1$–$C_4$)-alkylsulfonyl, aryl-($C_2$–$C_4$)-alkenylthio, aryl-($C_2$–$C_4$)-alkenylsulfinyl, aryl-($C_2$–$C_4$)-alkenylsulfonyl, aryl-($C_1$–$C_4$)-alkylamino, aryl-($C_3$–$C_4$)-alkenylamino, aryl-($C_1$–$C_6$)-dialkylsilyl, diaryl-($C_1$–$C_6$)-alkylsilyl, triarylsilyl and 5- or 6-membered heterocyclyl, where the cyclic moiety of the fourteen last-mentioned radicals is unsubstituted or substituted by one or more radicals selected from the group consisting of halogen, cyano, nitro, amino, hydroxyl, thio, ($C_1$–$C_4$)-alkyl, ($C_1$–$C_4$)-haloalk- yl, ($C_3$–$C_8$)-cycloalkyl, ($C_1$–$C_4$)-alkoxy, ($C_1$–$C_4$)-haloalkoxy, ($C_1$–$C_4$)-alkylthio, ($C_1$–$C_4$)-haloalkylthio, ($C_1$–$C_4$)-alkylamino, ($C_1$–$C_4$)-haloalkylamino and ($C_1$–$C_4$)-alkanoyl, and if $R^9$ is aryl or heterocyclyl, ($C_1$–$C_4$)-alkyl or $C_1$–$C_4$)-haloalkyl.

6. A compound of the formula (II) or a salt thereof

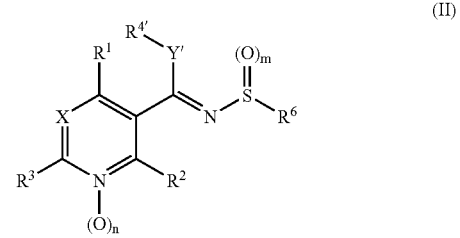

where the symbols and indices are as defined below:

X is =CH—;

Y'is —O— or —S—;

n is 0 or 1;

m is 0, 1 or 2;

$R^1$ is $SF_5$, $CHF_2$, $CF_2Cl$ or $CF_3$;

$R^2$, $R^3$ independently of one another are hydrogen, ($C_1$–$C_6$)-alkyl, ($C_1$–$C_6$)-haloalkyl or halogen, where one or two $CH_2$ groups may be replaced by —O— or —S— or —N($C_1$–$C_6$)-alkyl, with the proviso that heteroatoms may not be adjacent;

$R^{4'}$ is hydrogen, ($C_1$–$C_{10}$)-alkyl, ($C_3$–$C_{10}$)-cycloalkyl, ($C_3$–$C_{10}$)-alkenyl, ($C_3$–$C_{10}$)-alkynyl, ($C_6$–$C_{14}$)-aryl or ($C_3$–$C_{10}$)-heterocyclyl, where the radicals mentioned may be unsubstituted or mono- or polysubstituted; and $R^6$ is hydrogen, ($C_1$–$C_{10}$)-alkyl, ($C_3$–$C_{10}$)-alkenyl, ($C_3$–$C_{10}$)-alkynyl, ($C_3$–$C_8$)-cycloalkyl, ($C_4$–$C_8$)-cycloalkenyl, ($C_8$–$C_{10}$)-cycloalkynyl, aryl or heteroaryl, where the radicals mentioned may be unsubstituted or mono-or polysubstituted.

7. A compound of the formula (II)

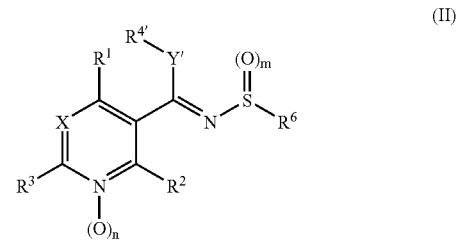

where X is =CH—, Y' is —O—, m and n are 0, $R^1$ is $CF_3$, $R^2$, $R^3$ and $R^{4'}$ are hydrogen and $R^6$ is ($C_1$–$C_{10}$)-alkyl, ($C_3$–$C_8$)-cycloalkyl, aryl, benzyl or heterocyclyl having a total of one to three nitrogen, oxygen and/or sulfur ring atoms, where the radicals mentioned may be unsubstituted or mono- or polysubstituted.

8. A compound of the formula (I) or a salt thereof as claimed in claim 5 where Y is =O, n is 0, $R^1$ is $CF_3$, $R^2$, $R^3$ and $R^4$ are hydrogen and the substituents are $R^7$ are identical or different $R^8$ or two radicals $R^7$ together with the atoms to which they are attached form a three- to eight-membered saturated or unsaturated ring system which is unsubstituted or substituted by one or more radicals $R^8$ and which may also contain further heteroatoms, selected from the group consisting of O, N, S, SO and $SO_2$; $R^8$ being as defined in claim 5.

9. A process for preparing compounds of the formula (I), which comprises the following steps:

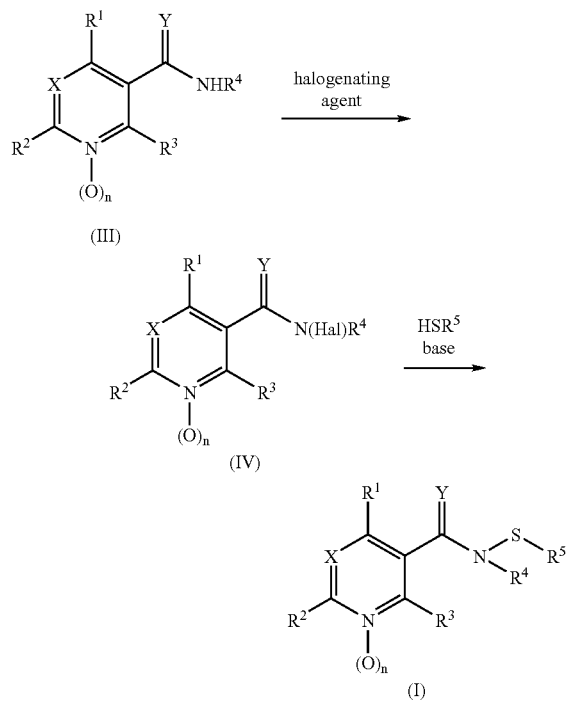

a) reaction of a carboxamide of the formula (III) with a halogenating agent to give a compound of the formula (IV), and
b) reaction of this compound with a thioether $R^5SH$ in the presence of a base to give the end products of the formula (I), where in these formulae the radicals $R^1$, $R^2$, $R^3$, $R^4$, $R^5$, X and Y and the index n have the meanings given in below:
X is =CH—;
Y is =O or =S;
n is 0 or 1;
$R^1$ is $(C_1-C_6)$-alkyl, $(C_1-C_6)$-haloalkyl, —S(halogen)$_5$ or halogen, where one or two $CH_2$ groups may be replaced by —O— or —S— or —N$(C_1-C_6)$-alkyl, with the proviso that heteroatoms may not be adjacent;
$R^2$, $R^3$ independently of one another are hydrogen, $(C_1-C_6)$-alkyl, $(C_1-C_6)$-haloalkyl or halogen, where one or two $CH_2$ groups may be replaced by —O— or —S— or —N$(C_1-C_6)$-alkyl, with the proviso that heteroatoms may not be adjacent;
$R^4$ is hydrogen, $(C_1-C_{10})$-alkyl, $(C_3-C_{10})$-cycloalkyl, $(C_3-C_{10})$-alkenyl, $(C_3-C_{10})$-alkynyl, $(C_6-C_{14})$-aryl, $(C_3-C_{10})$-heterocyclyl or $(C_1-C_{10})$-alkanoyl, where the radicals mentioned may be unsubstituted or mono- or polysubstituted;
$R^5$ is hydrogen, $(C_1-C_{10})$-alkyl, $(C_3-C_{10})$-alkenyl, $(C_3-C_{10})$-alkynyl, $(C_3-C_8)$-cycloalkyl, $(C_4-C_8)$-cycloalkenyl, $(C_8-C_{10})$-cycloalkynyl, aryl or heterocyclyl, where the radicals mentioned may be unsubstituted or mono- or polysubstituted.

10. A process for preparing compounds of the formula (I) as claimed in claim 1, which comprises reacting an activated derivative of the carboxylic acid or thiocarboxylic acid of the formula (VI)

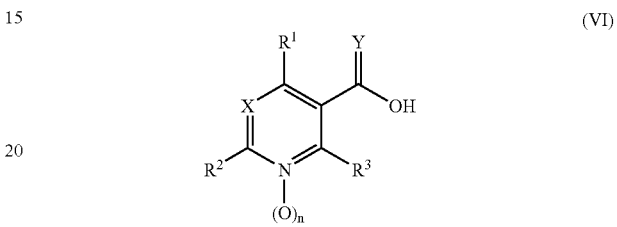

in the presence of a base with a compound of the formula (VII)

where in these formulae the radicals $R^1$, $R^2$, $R^3$, $R^4$, $R^5$, X and Y and the indices m and n have the meanings given in claim 1.

11. A process for preparing compounds of the formula (Ia) by thermal decomposition of the sulfimides of the formula (VIII)

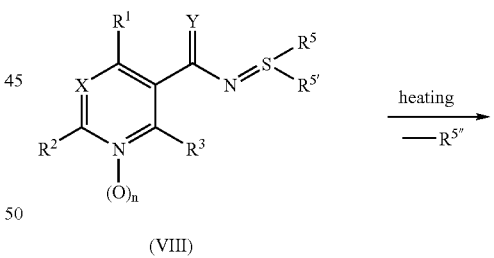

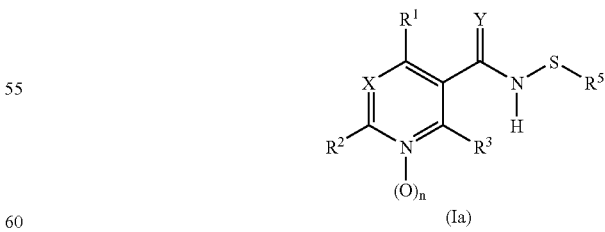

where the radicals $R^1$, $R^2$, $R^3$, $R^5$, X and Y and the index n are as defined below:
X is =CH—;
Y is =O or =S;
n is 0 or 1;

$R^1$ is $(C_1-C_6)$-alkyl, $(C_1-C_6)$-haloalkyl, —S(halogen)$_5$ or halogen, where one or two CH$_2$ groups may be replaced by —O— or —S— or —N(C$_1$–C$_6$)-alkyl, with the proviso that heteroatoms may not be adjacent;

$R^2$, $R^3$ independently of one another are hydrogen, $(C_1-C_6)$-alkyl, $(C_1-C_6)$-haloalkyl or halogen, where one or two CH$_2$ groups may be replaced by —O— or —S— or —N(C$_1$–C$_6$)-alkyl, with the proviso that heteroatoms may not be adjacent;

$R_5$ is hydrogen, $(C_1-C_{10})$-alkyl, $(C_3-C_{10})$-alkenyl, $(C_3-C_{10})$-alkynyl, $(C_3-C_8)$-cycloalkyl, $(C_4-C_8)$-cycloalkenyl, $(C_8-C_{10})$-cycloalkynyl, aryl or heterocyclyl, where the radicals mentioned may be unsubstituted or mono- or polysubstituted;

$R^{5'}$ is one of the groups defined for $R^5$ having a β-hydrogen atom and $R^{5''}$ is the ethylenically unsaturated leaving group corresponding to $R^{5'}$ reduced by one hydrogen atom.

12. A process for preparing compounds of the formula (II), which comprises reacting the compounds of the formula (Ib)

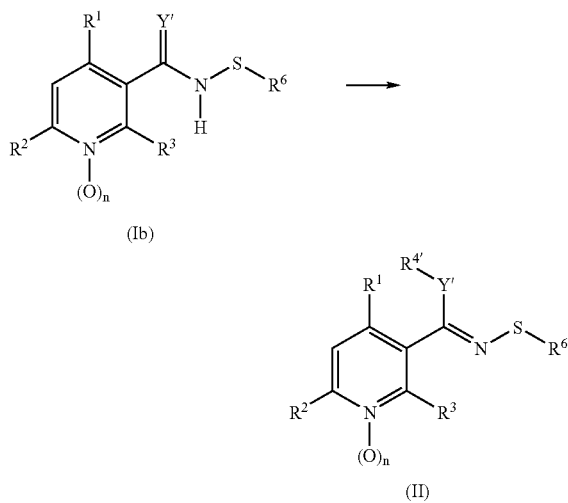

(Ib)

(II)

with an alcohol $R^{4'}$—OH in the presence of an azodicarboxylic acid diester and a phosphine in accordance with the scheme above to give the compounds of the formula (II) in which, $R^{4'}$ has one of the meanings below, except for H, and $R^1$, $R^2$, $R^3$, $R^6$, X, Y and n have one of the meanings defined below:

X is =CH—;
Y' is —O— or —S—;
n is 0 or 1;
$R^1$ is $(C_1-C_6)$-alkyl, $(C_1-C_6)$-haloalkyl, —S(halogen)$_5$ or halogen, where one or two CH$_2$ groups may be replaced by —O— or —S— or —N(C$_1$–C$_6$)-alkyl, with the proviso that heteroatoms may not be adjacent;

$R^2$, $R^3$ independently of one another are hydrogen, $(C_1-C_6)$-alkyl, $(C_1-C_6)$-haloalkyl or halogen, where one or two CH$_2$ groups may be replaced by —O— or —S— or —N(C$_1$–C$_6$)-alkyl, with the proviso that heteroatoms may not be adjacent;

$R^{4'}$ is hydrogen, $(C_1-C_{10})$-alkyl, $(C_3-C_{10})$-cycloalkyl, $(C_3-C_{10})$-alkenyl, $(C_3-C_{10})$-alkynyl, $(C_6-C_{14})$-aryl, $(C_3-C_{10})$-heterocyclyl or $(C_1-C_{10})$-alkanoyl, where the radicals mentioned may be unsubstituted or mono- or polysubstituted; and $R^6$ is hydrogen, $(C_1-C_{10})$-alkyl, $(C_3-C_{10})$-alkenyl, $(C_3-C_{10})$-alkynyl, $(C_3-C_8)$-cycloalkyl, $(C_4-C_8)$-cycloalkenyl, $(C_8-C_{10})$-cycloalkynyl, aryl or heterocyclyl, where the radicals mentioned may be unsubstituted or mono- or polysubstituted.

13. A composition having insecticidal, acaricidal, ixodicidal, nematicidal, molluscidal and/or fungicidal action, which comprises at least one compound of the formula (I) or a salt thereof and/or a compound of the formula (II) or a salt thereof as claimed in claim 1 or 2, respectively.

14. A method for controlling animal pests comprises the step of directly or indirectly applying to the pest a compound of the formula (I) or a salt thereof as claimed in claim 1.

15. A method for controlling animal pests comprises the step of directly or indirectly applying to the pest a compound of the formula (II) or a salt thereof as claimed in claim 2.

16. A method for warding off or fending off harmful organisms, where one or more compounds of the formula (I) or salts thereof as claimed in claim 1 are applied to the site from which the harmful organisms are to be fended off or warded off.

17. A method forwarding off or fending off harmful organisms, where one or more compounds of the formula (II) or salts thereof as claimed in claim 2 are applied to the site from which the harmful organisms are to be fended off or warded off.

18. A veterinary medicament comprising a compound of the formula (I) or a salt thereof as claimed in claim 1.

19. A veterinary medicament comprising a compound of the formula (II) or a salt thereof as claimed in claim 2.

* * * * *